United States Patent
Surushe et al.

(10) Patent No.: US 11,801,168 B2
(45) Date of Patent: Oct. 31, 2023

(54) TAPE-TYPE ABSORBENT ARTICLE WITH BELT STRUCTURE

(71) Applicant: The Procter & Gamble Company, Cincinnati, OH (US)

(72) Inventors: Abhishek Prakash Surushe, Schwalbach am Taunus (DE); Jeromy Thomas Raycheck, South Lebanon, OH (US); Kumardipti Chatterjee, Indian Hill, OH (US); Donald Carroll Roe, West Chester, OH (US); Russell Andrew Hayden, New Richmond, OH (US); Alejandro Jose Rivero, São Paulo (BR)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 16/684,895

(22) Filed: Nov. 15, 2019

(65) Prior Publication Data
US 2021/0145650 A1     May 20, 2021

(51) Int. Cl.
*A61F 13/15*     (2006.01)
*A61F 13/62*     (2006.01)

(52) U.S. Cl.
CPC .. *A61F 13/15585* (2013.01); *A61F 13/15699* (2013.01); *A61F 13/15723* (2013.01); *A61F 13/15747* (2013.01); *A61F 13/62* (2013.01)

(58) Field of Classification Search
CPC .......... A61F 13/15585; A61F 13/15699; A61F 13/15723; A61F 13/15747; A61F 13/62; A61F 13/64; A61F 13/15756
See application file for complete search history.

(56) References Cited

U.S. PATENT DOCUMENTS

D132,937 S    6/1942   Cadgene
3,658,064 A    4/1972   Pociluyko
(Continued)

FOREIGN PATENT DOCUMENTS

CN    101346118 A    1/2009
CN    102427786 A    4/2012
(Continued)

OTHER PUBLICATIONS

International Search Report and Written Opinion; Application Ser. No. PCT/US2020/070710; dated Mar. 2, 2021, 13 pages.
(Continued)

*Primary Examiner* — George R Koch
*Assistant Examiner* — Christopher C Caillouet
(74) *Attorney, Agent, or Firm* — Sarah M. DeCristofaro; Wednesday Shipp

(57) ABSTRACT

A method for providing successive individual combination belt structures each comprising a fastening component includes providing a machine-direction continuous strip of web material having a pair of machine-direction outer side edges, opposing side margin portions, and a cross-direction width therebetween. The web material is conveyed along the machine direction to fastening component process equipment to continuously affix successive fastening components to the web material. The web material is conveyed to cross-direction cutting equipment to cut individual combination front belt structures from the web material along predominately cross-direction cut lines.

17 Claims, 24 Drawing Sheets

(56) References Cited

U.S. PATENT DOCUMENTS

| | | |
|---|---|---|
| 3,848,594 A | 11/1974 | Buell |
| 3,860,003 A | 1/1975 | Buell |
| 4,610,678 A | 9/1986 | Weisman |
| 4,662,875 A | 5/1987 | Hirotsu |
| 4,673,402 A | 6/1987 | Weisman |
| 4,699,622 A | 10/1987 | Toussant |
| 4,808,178 A | 2/1989 | Aziz |
| 4,834,735 A | 5/1989 | Alemany |
| 4,834,741 A | 5/1989 | Sabee |
| 4,846,815 A | 7/1989 | Scripps |
| 4,888,231 A | 12/1989 | Angstadt |
| 4,892,536 A | 1/1990 | DesMarais et al. |
| 4,894,060 A | 1/1990 | Nestegard |
| 4,909,803 A | 3/1990 | Aziz |
| 4,946,527 A | 8/1990 | Battrell |
| 4,963,140 A | 10/1990 | Robertson |
| 4,990,147 A | 2/1991 | Freeland |
| 5,037,416 A | 8/1991 | Allen |
| 5,137,537 A | 8/1992 | Herron |
| 5,147,345 A | 9/1992 | Lavon |
| 5,151,092 A | 9/1992 | Buell |
| 5,156,793 A | 10/1992 | Buell et al. |
| 5,167,897 A | 12/1992 | Weber et al. |
| 5,221,274 A | 6/1993 | Buell |
| 5,242,436 A | 9/1993 | Weil |
| 5,260,345 A | 11/1993 | Desmarais |
| 5,269,775 A | 12/1993 | Freeland |
| 5,342,338 A | 8/1994 | Roe |
| 5,387,207 A | 2/1995 | Dyer |
| 5,397,316 A | 3/1995 | Young |
| 5,499,978 A | 3/1996 | Buell |
| 5,507,736 A | 4/1996 | Clear |
| 5,549,592 A | 8/1996 | Fries et al. |
| 5,554,145 A | 9/1996 | Roe |
| 5,569,234 A | 10/1996 | Buell |
| 5,571,096 A | 11/1996 | Dobrin |
| 5,580,411 A * | 12/1996 | Nease ............ A61F 13/49009 156/260 |
| 5,591,152 A | 1/1997 | Buell |
| D377,979 S | 2/1997 | Swenson et al. |
| 5,607,760 A | 3/1997 | Roe |
| 5,609,587 A | 3/1997 | Roe |
| 5,625,222 A | 4/1997 | Yoneda |
| 5,635,191 A | 6/1997 | Roe |
| 5,643,588 A | 7/1997 | Roe |
| D384,152 S | 9/1997 | Raufman |
| D403,400 S | 12/1998 | Dreier et al. |
| D403,401 S | 12/1998 | Dreier et al. |
| D403,402 S | 12/1998 | Dreier et al. |
| 5,851,205 A | 12/1998 | Hisada |
| 5,865,823 A | 2/1999 | Curro |
| 5,993,432 A | 11/1999 | Lodge et al. |
| 6,004,306 A | 12/1999 | Robles |
| D428,142 S | 7/2000 | Stromblad |
| 6,107,537 A | 8/2000 | Elder |
| 6,120,487 A | 9/2000 | Ashton |
| 6,132,410 A | 10/2000 | Van Gompel et al. |
| D435,103 S | 12/2000 | Schmoker |
| 6,195,850 B1 * | 3/2001 | Melbye ............ A61F 13/5622 24/304 |
| 6,248,097 B1 | 6/2001 | Beitz |
| D448,079 S | 9/2001 | Bruemmer-prestley |
| 6,336,922 B1 | 1/2002 | Vangompel et al. |
| 6,410,129 B2 | 6/2002 | Zhang |
| 6,432,098 B1 | 8/2002 | Kline et al. |
| 6,478,784 B1 | 11/2002 | Johnson |
| 6,677,258 B2 | 1/2004 | Carroll |
| 6,746,434 B2 | 6/2004 | Johnson |
| 6,843,134 B2 | 1/2005 | Anderson et al. |
| 6,945,968 B2 | 9/2005 | Svensson et al. |
| 7,062,983 B2 | 6/2006 | Anderson et al. |
| D543,276 S | 5/2007 | Martynus et al. |
| D544,098 S | 6/2007 | Martynus et al. |
| 7,435,243 B2 | 10/2008 | Miyamoto |
| D581,525 S | 11/2008 | Zink, II et al. |
| D583,469 S | 12/2008 | Zink, II et al. |
| 7,626,073 B2 | 12/2009 | Catalan |
| 7,744,576 B2 | 6/2010 | Busam |
| 7,750,203 B2 | 7/2010 | Becker |
| 7,806,883 B2 | 10/2010 | Fossum |
| 7,819,853 B2 | 10/2010 | Desai |
| 7,867,213 B2 * | 1/2011 | Bandorf ............ A61F 13/64 604/394 |
| 8,062,279 B2 | 11/2011 | Miyamoto |
| 8,145,338 B2 | 3/2012 | Kent |
| 8,145,343 B2 | 3/2012 | Debruler |
| 8,145,344 B2 | 3/2012 | Debruler |
| 8,227,071 B2 | 7/2012 | Wood et al. |
| 8,244,393 B2 | 8/2012 | Mclaughlin |
| 8,454,571 B2 | 6/2013 | Rezai |
| 8,618,350 B2 | 12/2013 | Mansfield |
| 8,663,186 B2 | 3/2014 | Lam et al. |
| 8,712,573 B2 | 4/2014 | Debruler |
| 8,712,574 B2 | 4/2014 | Debruler |
| 8,784,722 B2 | 7/2014 | Rocha |
| 8,795,809 B2 | 8/2014 | Mansfield |
| 8,939,957 B2 | 1/2015 | Raycheck et al. |
| 8,992,500 B2 | 3/2015 | Fujioka |
| 9,119,751 B2 | 9/2015 | Waksmundzki et al. |
| 9,138,362 B2 | 9/2015 | Popp |
| 9,265,673 B2 | 2/2016 | Stabelfeldt |
| 9,265,674 B2 | 2/2016 | Hancock-cooke |
| 9,301,889 B2 | 4/2016 | Miyamoto |
| 9,429,929 B2 | 8/2016 | Debruler |
| 9,468,265 B2 | 10/2016 | Horn |
| 9,468,569 B2 | 10/2016 | Hancock-cooke |
| 9,610,202 B2 | 4/2017 | Rezai et al. |
| 9,615,980 B2 | 4/2017 | Enz |
| 9,867,743 B2 | 1/2018 | Stabelfeldt |
| 9,962,296 B2 | 5/2018 | Mansfield |
| 9,980,859 B2 | 5/2018 | Popp |
| 10,034,802 B2 | 7/2018 | Macura et al. |
| D825,055 S | 8/2018 | Hirsch |
| 10,076,162 B2 | 9/2018 | Rocha |
| 10,085,897 B2 | 10/2018 | Landgrebe et al. |
| D879,972 S | 3/2020 | Caneppele et al. |
| D889,640 S | 7/2020 | Raycheck et al. |
| 10,798,997 B2 | 10/2020 | Rocha |
| 11,026,851 B2 | 6/2021 | Saito et al. |
| D928,310 S | 8/2021 | Chase et al. |
| D936,845 S | 11/2021 | Hahn et al. |
| 11,389,344 B2 | 7/2022 | Suyama |
| 11,399,990 B2 | 8/2022 | Suyama |
| 2002/0038110 A1 | 3/2002 | Kusibojoska et al. |
| 2002/0058923 A1 | 5/2002 | Suprise et al. |
| 2002/0193776 A1 | 12/2002 | Fernfors |
| 2003/0009144 A1 | 1/2003 | Tanzer et al. |
| 2003/0050616 A1 | 3/2003 | Reynolds et al. |
| 2003/0135192 A1 | 7/2003 | Guralski et al. |
| 2004/0082933 A1 | 4/2004 | Karami |
| 2004/0181200 A1 | 9/2004 | Desai |
| 2004/0193133 A1 | 9/2004 | Desai |
| 2005/0222552 A1 | 10/2005 | Otsubo |
| 2006/0129119 A1 | 6/2006 | Kistler |
| 2006/0178651 A1 | 8/2006 | Glaug |
| 2006/0212013 A1 | 9/2006 | Cohen et al. |
| 2006/0287637 A1 | 12/2006 | Lam |
| 2007/0000987 A1 | 1/2007 | Karlsson |
| 2007/0073260 A1 | 3/2007 | Roe |
| 2007/0219521 A1 | 9/2007 | Hird et al. |
| 2007/0249254 A1 | 10/2007 | Mansfield |
| 2007/0287983 A1 | 12/2007 | Lodge |
| 2007/0293111 A1 | 12/2007 | Mansfield |
| 2009/0157034 A1 | 6/2009 | Mattingly et al. |
| 2009/0258210 A1 | 10/2009 | Iyad |
| 2009/0299323 A1 | 12/2009 | Schlinz et al. |
| 2010/0180407 A1 | 7/2010 | Rocha |
| 2011/0073513 A1 | 3/2011 | Weisman et al. |
| 2011/0092947 A1 | 4/2011 | Kline |
| 2011/0106043 A1 | 5/2011 | Waksmundzki et al. |
| 2011/0139657 A1 | 6/2011 | Hird et al. |
| 2011/0139658 A1 | 6/2011 | Hird et al. |
| 2011/0139659 A1 | 6/2011 | Hird et al. |
| 2011/0152812 A1 | 6/2011 | Hird et al. |

(56) References Cited

U.S. PATENT DOCUMENTS

| | | |
|---|---|---|
| 2011/0155304 A1* | 6/2011 | Sakaguchi ........ A61F 13/15764 156/211 |
| 2011/0178486 A1 | 7/2011 | Beck et al. |
| 2011/0184372 A1 | 7/2011 | Esping |
| 2011/0208144 A1 | 8/2011 | Roe et al. |
| 2012/0095429 A1 | 4/2012 | Kobayashi |
| 2012/0316526 A1 | 12/2012 | Rosati et al. |
| 2013/0082418 A1 | 4/2013 | Curro et al. |
| 2013/0131625 A1 | 5/2013 | Schlinz |
| 2013/0226121 A1 | 8/2013 | Kikkawa et al. |
| 2013/0345657 A1 | 12/2013 | Nelson et al. |
| 2014/0000003 A1 | 1/2014 | Ashraf |
| 2014/0000070 A1 | 1/2014 | Ashraf |
| 2014/0000784 A1 | 1/2014 | Rane |
| 2014/0257227 A1 | 9/2014 | Roe |
| 2015/0032075 A1 | 1/2015 | Popp et al. |
| 2015/0032079 A1 | 1/2015 | Enz et al. |
| 2015/0045758 A1 | 2/2015 | Goodlander et al. |
| 2015/0126955 A1 | 5/2015 | Sauer et al. |
| 2015/0173963 A1* | 6/2015 | Coe .................. A61F 13/15723 156/73.1 |
| 2016/0250085 A1 | 9/2016 | Lavon et al. |
| 2016/0270977 A1 | 9/2016 | Surushe |
| 2016/0278994 A1 | 9/2016 | Martynus et al. |
| 2017/0056253 A1 | 3/2017 | Chester et al. |
| 2017/0056256 A1 | 3/2017 | Smith |
| 2017/0287893 A1 | 10/2017 | Rouviere et al. |
| 2017/0326006 A1 | 11/2017 | Neubauer et al. |
| 2018/0042777 A1 | 2/2018 | Dalal et al. |
| 2018/0042778 A1 | 2/2018 | Lenser et al. |
| 2018/0228253 A1 | 8/2018 | Emslander et al. |
| 2018/0243147 A1 | 8/2018 | Swedberg et al. |
| 2018/0271716 A1 | 9/2018 | Dalai |
| 2018/0271717 A1 | 9/2018 | Dria |
| 2018/0325753 A1* | 11/2018 | Vohwinkel ............ A61F 13/472 |
| 2019/0060135 A1 | 2/2019 | Kawka |
| 2020/0054505 A1 | 2/2020 | Su et al. |
| 2020/0113749 A1 | 4/2020 | Surushe et al. |
| 2020/0179184 A1 | 6/2020 | Kaiser |
| 2021/0145660 A1 | 5/2021 | Surushe et al. |
| 2021/0145661 A1 | 5/2021 | Surushe et al. |
| 2021/0145662 A1 | 5/2021 | Hayden et al. |
| 2021/0145663 A1 | 5/2021 | Hayden et al. |
| 2021/0251824 A1 | 8/2021 | Roe |
| 2021/0386602 A1 | 12/2021 | Raycheck et al. |
| 2022/0257432 A1 | 8/2022 | Raycheck et al. |

FOREIGN PATENT DOCUMENTS

| | | |
|---|---|---|
| CN | 103260569 A | 8/2013 |
| CN | 104302261 A | 1/2015 |
| CN | 105431122 A | 3/2016 |
| CN | 105919731 A | 9/2016 |
| CN | 206910449 U | 1/2018 |
| EP | 1377214 B1 | 4/2005 |
| EP | 2259763 B1 | 6/2014 |
| JP | H11155906 A | 6/1999 |
| JP | 2004508138 A | 3/2004 |
| JP | 2006246999 A | 9/2006 |
| JP | 2007521036 A | 8/2007 |
| JP | 2009056001 A | 3/2009 |
| JP | 2014138889 A | 7/2014 |
| WO | 9108725 A | 6/1991 |
| WO | 9516746 A1 | 6/1995 |
| WO | 0015069 A1 | 3/2000 |
| WO | 0156526 A1 | 8/2001 |
| WO | 2005016211 A1 | 2/2005 |
| WO | WO2005110731 A2 | 11/2005 |
| WO | 2011129097 A1 | 10/2011 |
| WO | 2015015334 A1 | 2/2015 |
| WO | WO2016022629 A1 | 2/2016 |
| WO | WO2019018721 A1 | 1/2019 |
| WO | 2019145647 A1 | 8/2019 |
| WO | 2020041271 A1 | 2/2020 |

OTHER PUBLICATIONS

Unpublished U.S. Appl. No. 16/684,860, filed Nov. 15, 2019, to Abhishek Prakash Surushe et al.
Unpublished U.S. Appl. No. 29/713,366, filed Nov. 15, 2019, to Abhishek Prakash Surushe et al.
All Office Actions; U.S. Appl. No. 16/538,865.
All Office Actions; U.S. Appl. No. 16/684,860.
AH Office Actions, U.S. Appl. No. 29/713,366.
Definition of "integral," www.dictionary.com, Apr. 20, 2023, pp. 5.

* cited by examiner

TAPE-TYPE ABSORBENT ARTICLE WITH BELT STRUCTURE

FIELD OF THE INVENTION

The present disclosure relates to absorbent articles having belts and/or fastening systems.

BACKGROUND OF THE INVENTION

Improvements in manufacturing techniques and developments in materials technologies have allowed manufacturers of disposable diapers to reduce the quantities of materials used in manufacture and reduce the size, bulk and/or weight of various components of such products. For example, the development and improvement of superabsorbent polymers (also known as absorbent gelling materials), and improvements in absorbent core designs, have enabled manufacturers to reduce the size and bulkiness of absorbent core components. Improvements in polymer materials and processing techniques have enabled manufacturers to use lower basis weight components including lower basis weight nonwoven web materials and film materials. This has enabled per-unit savings in costs of materials and shipping, without compromising the absorbency or containment functions of the products.

As a result of these improvements, current diaper designs, while relatively light, non-bulky and economical, also may have attributes perceived negatively by some consumers. In some current designs, the upper waist regions of the diapers may have relatively little or no absorbent material and may consist only of a few layers of relatively low basis weight, thin web materials. In such current designs, the upper waist regions may have an insubstantial, flimsy feel to the consumer. Additionally, with reduction of materials basis weights (and associated reduction of caliper), the upper waist regions may be less stiff than those of other/earlier products, and thereby less supportive of traditional fastening systems and more prone to wrinkling, flipping or sagging on the wearer, particularly when the diaper is loaded with the weight of the wearer's exudates and/or the wearer is relatively active.

Consequently, any cost-effective methods and/or features for improving the waist region structure and the fastening systems may provide the manufacturer of the product a competitive advantage.

SUMMARY OF THE INVENTION

A method for providing successive individual combination belt structures each comprising a fastening component may include the steps of providing a machine-direction continuous strip of web material having a pair of machine-direction outer side edges, opposing side margin portions, and a cross-direction width therebetween; and conveying the web material along the machine direction to fastening component process equipment. The fastening component equipment may be operated to continuously affix successive fastening components to the web material as it moves along the machine direction. The web material may be conveyed to cross-direction cutting equipment, which may be operated to cut individual combination belt structures from the web material along predominately cross-direction cut lines, each combination belt structure comprising at least one of the affixed fastening component.

A method for providing successive individual front belt structures for diapers may include steps of providing a machine-direction continuous strip of web material having a pair of machine-direction outer side edges and a cross-direction width therebetween; and conveying the web material along the machine direction to folding equipment. The folding equipment may be used to continuously fold over opposing side margin portions of the web material in the cross direction about machine-direction fold lines. The web material may be conveyed the folded-over side margins to cross-direction cutting equipment, which may be operated to cut individual front belt structures from the web material along predominately cross-direction cut lines, each front belt structure comprising cut portions of the folded-over side margins.

A method for providing successive combination belt structures for diapers may include providing a machine-direction continuous strip of web material having a pair of machine-direction outer side edges and a cross-direction width therebetween; and conveying the web material along the machine direction to profiled side edge cutting equipment. The profiled side edge cutting equipment may be operated to cut successive pairs of profiled side edges between the pair of machine-direction outer edges, wherein each profiled side edge comprises a first convexity, a second convexity and a concavity disposed between the first and second convexities. The web material may be conveyed to cross-direction cutting equipment, which may be operated to cut individual combination belt structures from the web material along predominately cross-direction cut lines, each combination belt structure comprising profiled side edges.

DETAILED DESCRIPTION OF THE INVENTION

Figure 1A:
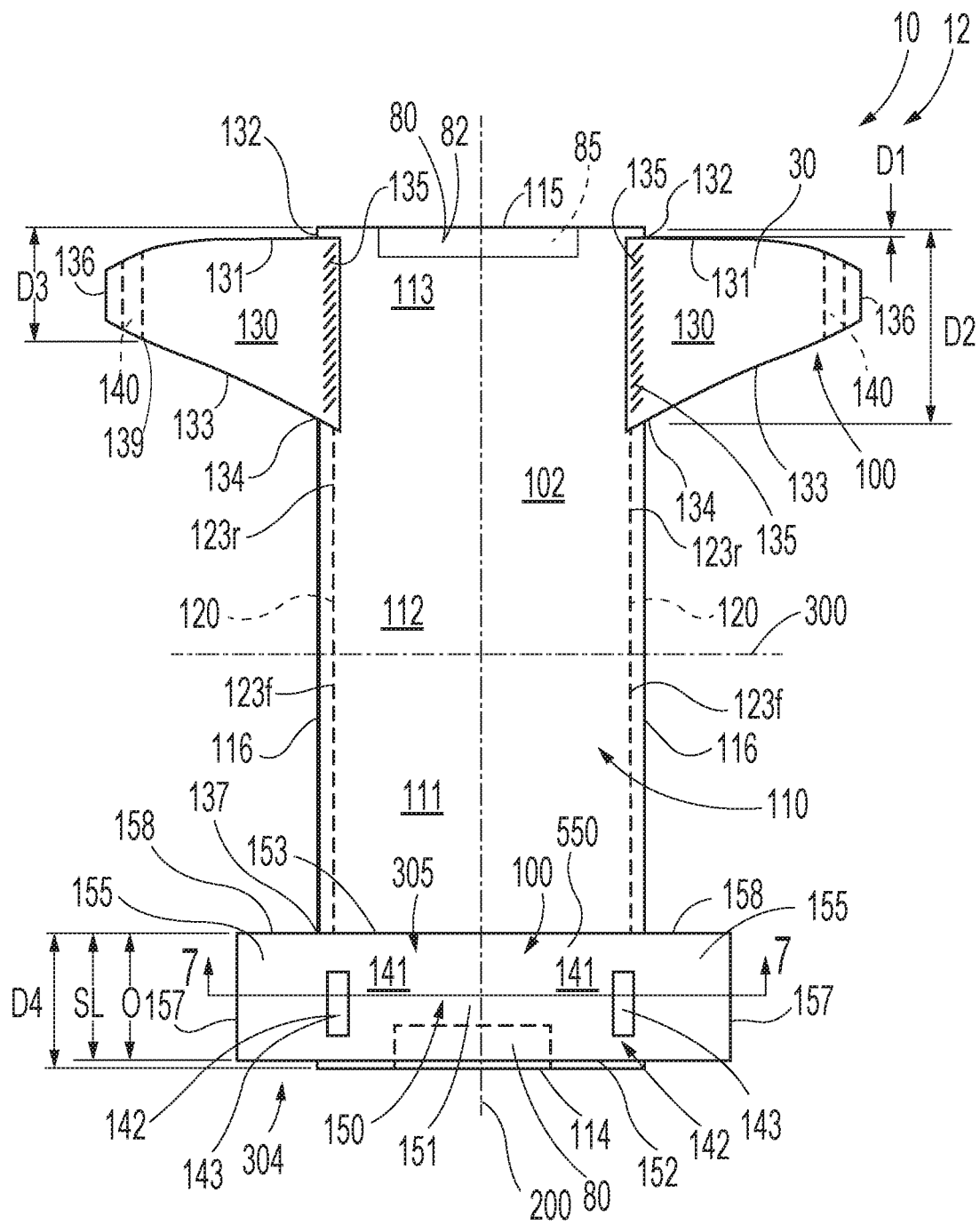
FIG. 1A is a schematic plan view of an example of a diaper, outward-facing surfaces facing the viewer.

"Absorbent article" means a device that absorbs and contains body exudates and, more specifically, devices that are placed against or in proximity to the body of the wearer to absorb and contain the various exudates discharged from the body. Exemplary absorbent articles include diapers, refastenable diapers or pant-type diapers, incontinence briefs and undergarments, diaper holders and liners, feminine hygiene garments such as panty liners, absorbent inserts, and the like.

"Disposed" refers to an element being located in a particular place or position. A feature that is disposed on a surface or side of a component may be integral with said component or may be joined to said component.

"Elastic" and "elastomeric" mean the ability of a material to stretch by at least 100% without rupture or breakage at a given load, and upon release of the load the elastic material or component exhibits at least 70% recovery (i.e., has less than 30% set) in one of the directions as per the Hysteresis Test described herein. Stretch, sometimes referred to as strain, percent strain, engineering strain, draw ratio, or elongation, along with recovery and set may each be determined according to the Hysteresis Test described in more detail below. Materials that are not elastic are referred to as inelastic.

"Integral with" a component means being formed from or formed by said component, or portions thereof, as opposed to being joined to the component.

"Joined" means configurations whereby an element is directly secured to another element by affixing the element directly to the other element, and configurations whereby an element is indirectly secured to another element by affixing the element to intermediate member(s) that in turn are affixed to the other element.

"Longitudinal" means a direction lengthwise in a component such that the longitudinal direction runs parallel to the maximum linear dimension in the x-y plane of the component. In an absorbent article as described herein, the longitudinal direction runs substantially perpendicular from a waist end edge to an opposing waist end edge when the absorbent article is in a flat out, uncontracted state, or from a waist end edge to the bottom of the crotch in a bifolded article.

"Lateral" refers to a direction generally perpendicular to the longitudinal direction. In the absorbent article described herein, the lateral direction runs substantially parallel from a side edge to an opposing side edge.

"Length" refers to a dimension in the longitudinal direction. The "width" of a feature is its dimension in the lateral direction.

"Inboard," with respect to a first feature of an article and its position relative a second feature or location on the article, means that the first feature lies closer to a respective axis of the article than the second feature or location, along a horizontal x-y plane approximately occupied by the article when laid out flat, extended to the full longitudinal and lateral dimensions of its component web materials against any contraction induced by any included pre-strained elastomeric material, on a horizontal surface. Laterally inboard means the first feature is closer to the longitudinal axis, and longitudinally inboard means the first feature is closer to the lateral axis. Conversely, "outboard," with respect to a first feature of an article and its position relative a second feature or location on the article, means that the first feature lies farther from the respective axis of the article than the second feature or location.

"Machine direction," with respect to a material or assembly of materials moving through a processing or manufacturing line, means a direction parallel to the direction of movement through the line. "Cross direction" means a direction perpendicular to the direction of movement through the line.

The "outward-facing" surfaces of a diaper or a component thereof are the surfaces that face away from the wearer when the diaper is worn.

"Registration," "register," "registered," or "registering" refer to a machine control process or system for controlling the placement of objects (e.g., indicia, ears, fastening components) on a substrate or laminate at target positions. Target positions may be determined by preset intervals and/or relative to specific locations or features disposed on the substrate or laminate.

The "wearer-facing" surfaces of a diaper or a component thereof are the surfaces that face toward the wearer when the diaper is worn.

Figure 1B:
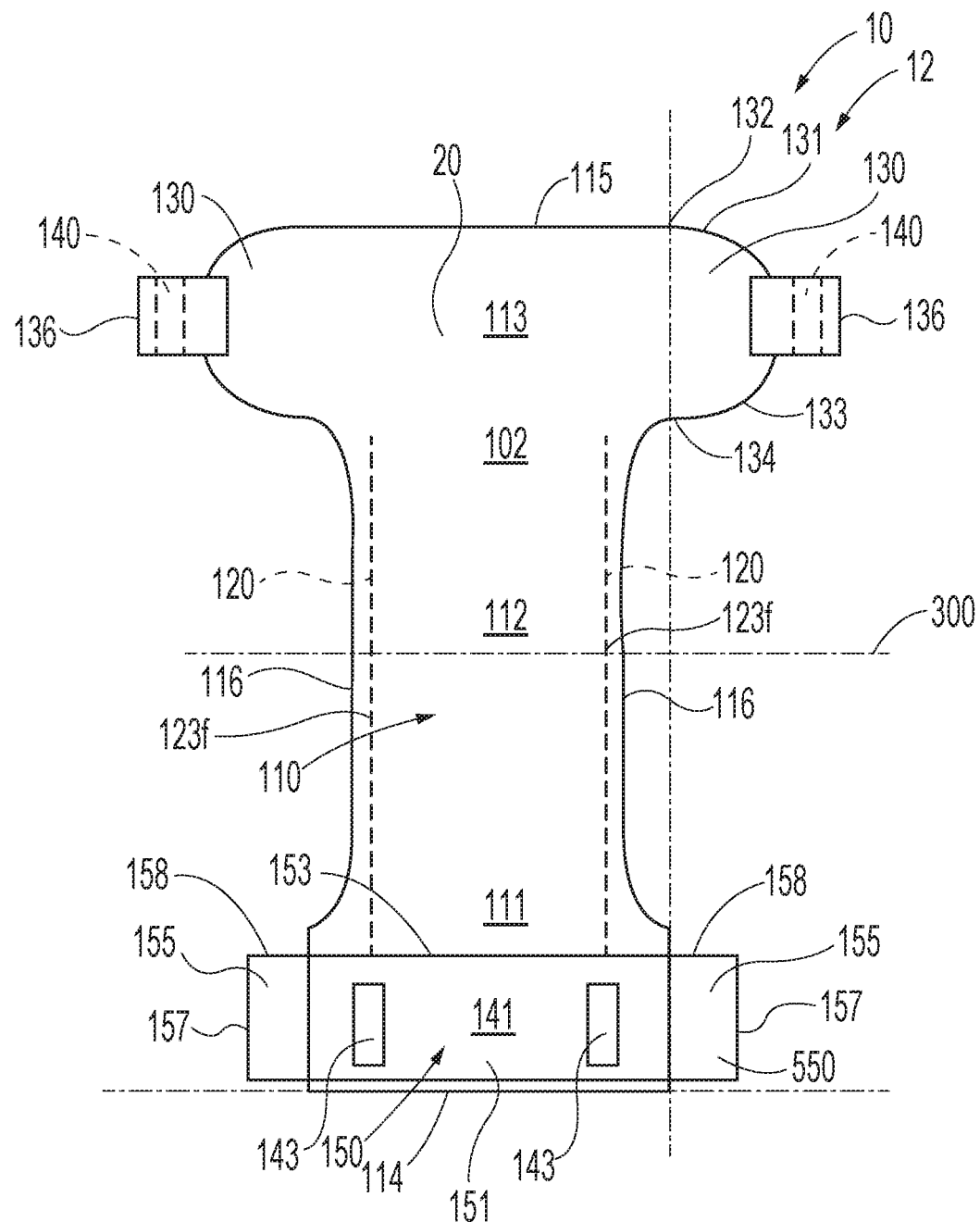
FIG. 1B is a schematic plan view of another example of diaper, outward-facing surfaces facing the viewer.
Figure 1C:
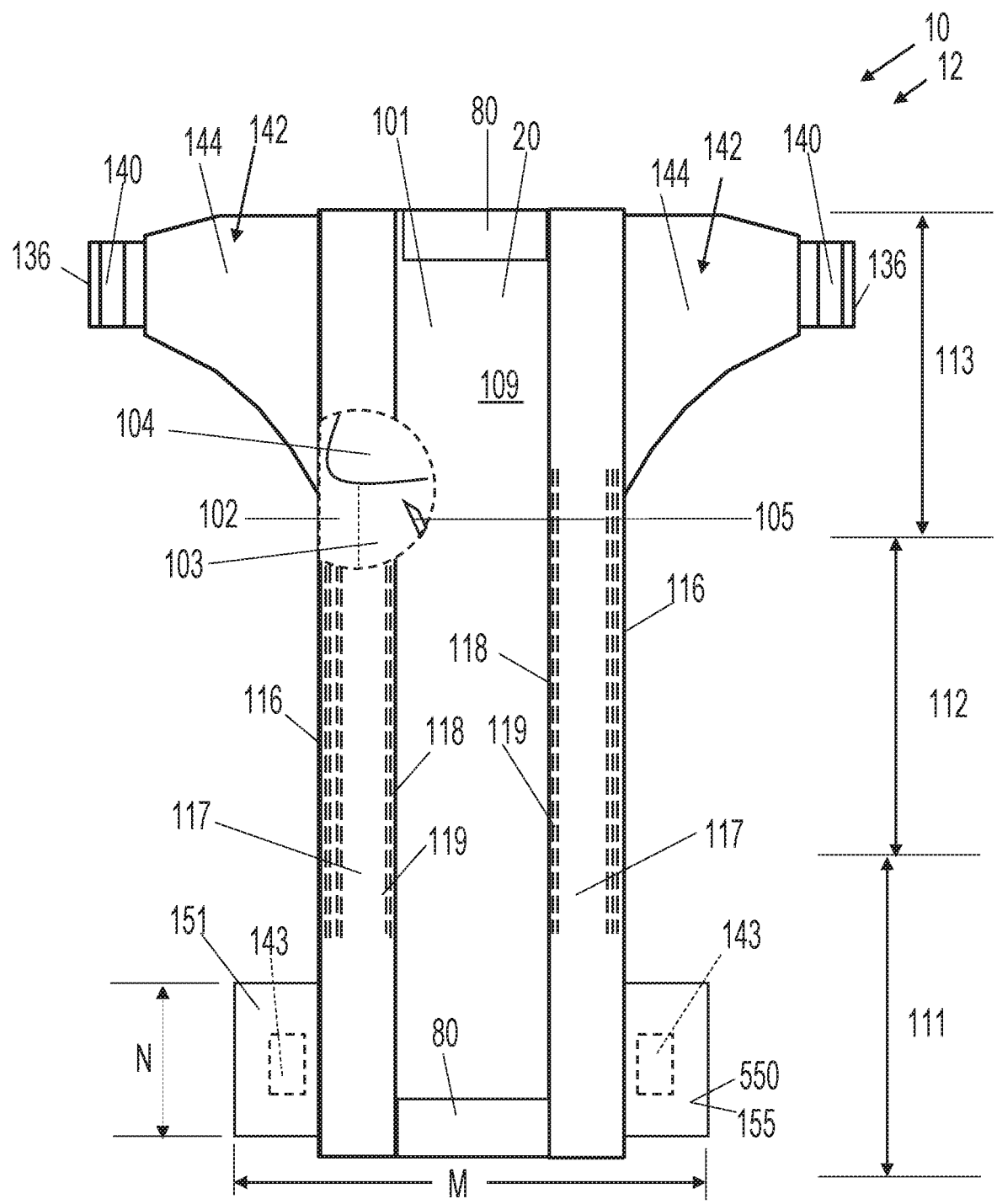
FIG. 1C is a schematic plan view of another example of diaper, wearer-facing surfaces facing the viewer.

FIGS. 1A-1B are plan views of an exemplary, nonlimiting examples of an absorbent article 10 in the form of a diaper 12, shown on the outward-facing side 110. The absorbent article may be disposable. FIG. 1C is a plan view of an exemplary, nonlimiting example of a diaper 12 with the wearer-facing side 109 facing the viewer. As shown in FIG. 1C, the absorbent article 10 comprises a chassis 20 formed of a liquid permeable topsheet 101, a liquid impermeable backsheet 102, and an absorbent core 103 disposed therebetween. The article 10 may further include an acquisition distribution system 104 disposed between the topsheet and absorbent core. In some nonlimiting examples, the absorbent core includes one or more channels 105.

The article 10 and chassis 20 have a front waist region 111, a rear waist region 113 opposed to the front waist region 111, and a crotch region 112 located between the front waist region 111 and the rear waist region 113. The article 10 includes a longitudinal centerline 200 and a lateral centerline 300. The outer periphery of the article 10 is defined by longitudinal edges 116 and waist edges (front waist edge 114 in front waist region 111 and rear waist edge 115 in rear waist region 113). The article 10 may have opposing longitudinal edges 116 that are oriented generally parallel to the longitudinal centerline 200. However, for better fit, longitudinal edges 116 may be curved or angled to produce, for example, an "hourglass" shape article when viewed in a plan view as shown in FIG. 1B.

Returning to FIG. 1C, one or more cuff structures 117 may be disposed on the wearer-facing side and may have portions affixed thereto by any suitable mechanism. Cuff structures 117 may have any form known for disposable diapers, and are variously known as barrier cuffs, standing cuffs, barrier leg cuffs, longitudinal cuffs, barrier flaps, etc. In some examples, the cuff structures 117 may have the configurations and materials described in, for example, U.S. Pat. Nos. 8,939,957 and 6,248,097. Free distal edges 118 of cuff structures 117 may have longitudinally-oriented elastic strands, strips or other cuff elastic members 119 disposed therealong, contraction of which will cause the cuff structures to gather longitudinally along their free edges 118 and provide a gasketing barrier along the wearer's body through the crotch region 112 to help contain exudates. The cuff elastic members 119 may be disposed in the cuff structures in a longitudinally pre-strained condition.

The article may comprise one or more waist features 80, which may be disposed in the front and/or rear waist regions. In some nonlimiting examples, one or both of the article's waist edges 115, 114 may be at least partially defined by a waist feature as illustrated in FIG. 1C. In further nonlimiting examples, a waist feature may be disposed inboard of the closest waist edge. A waist feature may be integral with one or more layers of the chassis, cuff structures and/or other elements in the waist region, or may be joined to one or more layers of the chassis, leg cuff structures and/or other elements disposed in the waist region. The waist feature may be joined between layers (FIG. 1A in front waist region), on the outward-facing surface 110 of the article (FIG. 1A in rear waist region), or on the wearer-facing surface 109 of the article (FIG. 1C). The waist feature may be extensible or elastic. An elasticized waist feature 82 is generally intended to expand and contract to dynamically fit the wearer's waist. Elasticized waist features include waistbands, waist cuffs having pockets formed from a portion of the waist feature that is unattached from the chassis, and waist panels designed to fit securely about the abdomen of the wearer. Nonlimiting examples of elasticized waist features are disclosed in U.S. patent application Ser. Nos. 14/533,472; 15/074,675 and 62/855,001. Elasticized waist features may comprise one or more nonwoven layers and one or more elastic elements 85. In nonlimiting examples, the elasticized waist feature comprises elastic strands joined to the nonwoven layer(s). In further nonlimiting examples, the elasticized waist feature comprises a laminate of one or more nonwoven layers and one or more films.

In alternative embodiments, the waist feature may be inelastic. In such configurations, the waist feature may provide additional anchoring about the waist of the wearer.

A waist feature can be used in conjunction with an ear to provide desirable stretch and flexibility, or otherwise enhance fit of the article on the wearer.

Longitudinal edges 116 may be formed of the longitudinal edges of any of the backsheet 102, topsheet 101, laterally outboard portions of cuff structures 117, or a layered combination of any of these. Longitudinal edges 116 may be cut and/or contoured as suggested in FIG. 1B, or may be straight as suggested in FIG. 1A. Longitudinal edges 116 also may have longitudinally-oriented elastic strands, strips or other leg band elastic members 120 disposed therealong, to cause the longitudinal edges 116 to gather about the wearer's legs, as shown in FIG. 1B. For example, leg band elastic members 120 may be sandwiched between the topsheet 101 and the backsheet 102, or between the material forming the cuff structures 117 and the backsheet 102, between the material forming the cuff structures 117 and the topsheet 101, or within a fold or layers of material forming the cuff structures 117, proximate to the longitudinal edges. The leg band elastic members 120 may be disposed along the longitudinal edges 116 in a pre-strained condition.

Fastening System(s)

Returning to FIG. 1A, the article 10 may include a fastening system 100, which may comprise a fastening component 140 disposed on a base member 130 in the rear waist region 113. In nonlimiting examples, the article may include a pair of base members, respectively extending laterally away from the longitudinal edges, and away from the longitudinal axis 200 of the diaper in the rear waist region 113, and a pair of fastening components 140 disposed proximate to opposite longitudinal edges. Base members 130 may be formed of continuous lateral extensions of the material forming backsheet 102 and/or topsheet 101 as suggested in FIGS. 1B-1C; or, as suggested in FIG. 1A, may each be formed of a separate piece of material that is affixed to the chassis, for example, to the topsheet 101 and/or the backsheet 102, at attachment locations via chassis attachment bonds 135. Chassis attachment bonds 135 may be present to bond the base members to materials of one or more of the topsheet, backsheet and cuff structure via heat and/or compression (causing a mechanical intertangling and/or intermixing and fusing of materials), adhesive, or any combination thereof. Base members 130 may be affixed to the outward-facing side of the backsheet 102, or to the wearer-facing side of the topsheet 101, or to a wearer-facing side of material forming the cuff structures 117. Alternatively, base members 130 may be sandwiched between the layers of the chassis 20 or between the chassis and cuff structure. A base member 130 may be in the form an ear 30, such that the base member 130 extends laterally outboard of the longitudinal edge 116 in the crotch region, as shown for example in FIG. 1A.

A base member may comprise on or more polymeric layers. In a non-limiting example, base members 130 may be formed of a material configured to exhibit elastic stretch and contraction in the lateral direction, enhancing comfort and secure fit of the diaper about the wearer. The base member may comprise an elastic laminate, which may comprise a combination including an elastomeric polymeric material (such as a film, or laterally-oriented strips or strands formed of elastomeric polymer) layered, laminated or interspersed with one or more layers of nonwoven material. In some examples, the base member may comprise a laminate of an elastomeric film sandwiched between two layers of nonwoven material. Suitable laminate materials are described in, for example, PCT Application No. WO2005/110731, and U.S. Application Publication Nos. US2011/0092947; US2007/0293111; US2004/0181200 and US2004/0193133. The base member 130 may comprise a gathered laminate, wherein one of the layers is strained to a greater degree than a remaining layer during lamination and/or bonding. In this way, the less extensible layer (i.e., a nonwoven) will form gathers when the laminate is in a relaxed state. Corrugations then form in the nonwoven layer(s) when the subsequently formed laminate is in a relaxed state. The base member may comprise an ultrasonically bonded laminate as is disclosed for example in U.S. Pat. Pub. Nos. 2018/0042777, 2018/0042778; 2018/0271716; and 2018/0271717. Alternatively, the base member 130 may be activated by processes disclosed in U.S. Pat. Pub. No. 2013/0082418, U.S. Pat. Nos. 4,834,741; 5,167,897; 5,993,432; 5,156,793; 5,167,897; 7,062,983 and 6,843,134 for example.

Still referring to FIGS. 1A-1C, the article may comprise a primary fastening system 100, which includes a primary first component 140. In nonlimiting examples, the diaper may include a pair of primary first components 140 each disposed respectively on a wearer-facing side of one of respective left and right base members 130. The primary fastening system also may comprise one or more primary second components 141 disposed on an outward-facing side of the front waist region 111. The primary first component is operatively engageable with the primary second component such that the primary fastening system secures the article about the waist and/or hip of the wearer. Nonlimiting examples of engageable fastening components include tape tabs, hook and loop fastening components, interlocking fasteners such as tabs & slots, buckles, buttons, snaps, and/or hermaphroditic fastening components. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The primary first component and/or the primary second component may further include a release tape or other material that protects the component from insult prior to use. In nonlimiting examples, the primary first component and/or the base member is foldable and may be folded prior to use such that the primary first component engages with material (e.g., base member material) that protects it from insult.

A base member 130 may terminate at a distal end 136 via a section of tape, strip or other suitable end member affixed to the main portion of the base member 130. Alternatively, the end portion of the base member 130 may simply be formed of extension(s) of one or more of the material(s) forming the main portion of base member 130. Each base member 130 may have a primary first component 140 disposed thereon proximate to distal end 136, attached thereto by adhesive, thermal and/or compression bonding or any other suitable attachment mechanism. Primary first component 140 may be any suitable type of fastening component configured to fastenably engage an outward-facing surface of the diaper at a landing zone 150 disposed in the front waist region 111. In a nonlimiting example, primary first component 140 may be a patch of hooks, and landing zone 150 may be defined by and/or be formed of a material adapted to receive and fastenably engage the hooks, thereby providing the primary second component 141 in a hook-and-loop fastening system. Primary second component 141 may be formed of a section of web material 151 overlying the backsheet to the outward-facing side thereof. In particular non-limiting examples, the section of web material 151 may be a nonwoven web material. The nonwoven web material formed of bicomponent or multicomponent fibers such as, for example, described in U.S. Pat. No. 9,468,265; U.S. Pat. Pub. Nos. 2014/0000784; 2014/000070 and US2014/0000003. It may be desirable that the force required to detach the primary first component from the web material 151 be at least about 20 N shear force to ensure secure and prolonged fastening. In further nonlimiting examples, the section of web material 151 may comprise a film or a laminate of nonwoven and film material.

In some examples, the primary first component 140 may be separately applied sections or patches of hooks material that are bonded by heat, compression, adhesive, ultrasonic bonding or any combination thereof. In other examples, primary first components may be patches of hooks that are formed directly on a section of the base member, more particularly formed directly on a section of a polymeric layer of the base member. For example, the hooks may be produced via application of molten polymer resin onto the layer, and subsequent formation of hooks in and from the melted, applied resin via known methods. The primary first components may be integrally formed from the polymeric material by heating and softening a portion of the material and pressing it into hook-forming cavities, as is disclosed in U.S. Pat. No. 8,784,722. The primary first components may be integrally formed from the polymeric material through a single continuous process as is disclosed in commonly assigned U.S. patent application Ser. No. 16/545,425.

Many disposable diapers currently marketed include front ears 155, laterally extending from the front waist portion of the diaper near the front waist edge, proximate to and/or extending from the left and right longitudinal edges. Front ears serve to provide the caregiver a laterally protruding front portion of the diaper to easily grasp and tug along each side, facilitating fastening of each fastening member 130 to the landing zone 150 of the front waist region. Front ears also serve to provide additional coverage of the wearer's skin in the hip regions. Current designs have front ears which are either extensions of one or more of the backsheet and topsheet materials, or alternatively, are formed of separate sections of material bonded to one or more of the topsheet, backsheet and/or cuff structure so as to extend laterally from the left and right sides of the main chassis.

Where the front ears are extensions of one or more of the backsheet and topsheet materials, manufacturing necessarily includes a profiled cutting of these materials to provide the extending front ear portions, and associated material waste. When the front ears are formed of separate sections of material bonded to one or more of the topsheet, backsheet and/or cuff structure, manufacturing must include steps associated with placing and bonding these front ear components to the chassis.

As an alternative, however, a section of web material 151 may be selected so as to be suitable for not only serving as the primary second component 141, but also for forming and providing one or more front ears 155, when cut to a size which allows for the section of web material 151 to extend laterally beyond the chassis along the longitudinal side(s). In some nonlimiting examples, at least a portion of the web material 151 may be adapted to receive and fastenably engage hooks included as or with primary first components 140, and thereby serve as the loops component of a hook-and-loop primary fastening system. In further examples, a portion of the nonwoven web material may be pattern bonded in a pattern of thermal bonds configured to enhance the strength and reliability of the material and of the loops structures it provides, as well as the fastening properties of the material. Suitable pattern bonding is disclosed in U.S. patent application Ser. No. 16/575,424.

This dual use of such a section of web material 151 can serve to both provide or support a suitable primary second component 141 and provide front ears 155, eliminating the need for other configurations and steps for providing front ears as described above. Additionally, the inclusion of the section of web material 151 to supplement the other materials of the chassis provides apparent and actual added lateral tensile strength, bending resistance, caliper and robustness to the front waist region.

The section of web material 151 that both (i) provides and/or supports a second component 141 of a fastening system and (ii) forms one or more ears 155, will also be referred to as "a combination belt structure" 550 herein.

As shown in FIG. 1C, the combination belt structure may comprise a maximum longitudinal length, N, of about 30 mm to about 100 mm, or from about 35 mm to about 90 mm, or from about 40 mm to about 85 mm, reciting for each range every 1 mm increment therein. The combination belt structure may comprise a maximum lateral width, M, from about 100 mm to about 500 mm, or from about 150 mm to about 400 mm, or from about 180 mm to about 300 mm, reciting for each range every 1 mm increment therein.

The combination belt structure may be bonded or adhered to an outward-facing surface of the backsheet 102 or other material forming an outward-facing surface of the diaper in the front waist region 111, by any suitable bonding mechanism including, for example, adhesive material(s). In some embodiments, the bonding pattern should not exceed backsheet edge 116 and preferably ends inboard of longitudinal edge 116 to avoid exposing adhesive to the wearer's skin. Additionally, or alternatively, the web material 151 may be decoupled from the chassis and/or other material that forms the outward-facing surface of the diaper in one or more areas in the front waist region. In the nonlimiting example shown in FIGS. 2-2A, the layers of the belt structure and chassis may be joined in an anchoring zone 316, which is bounded by a perimeter P. Outside of said perimeter, the layers may be unattached, attached in a weaker and/or more extensible manner than in the anchoring zone (e.g., activated to increase extensibility), thereby creating a decoupled zone 314. The decoupled zone is adjacent to one or more portions of the perimeter. The perimeter may comprise substantially straight portions and/or curvilinear portions. In some nonlimiting examples, straight portions may be disposed at angle of 5-89° with respect to the lateral or longitudinal axis.

Figure 3:
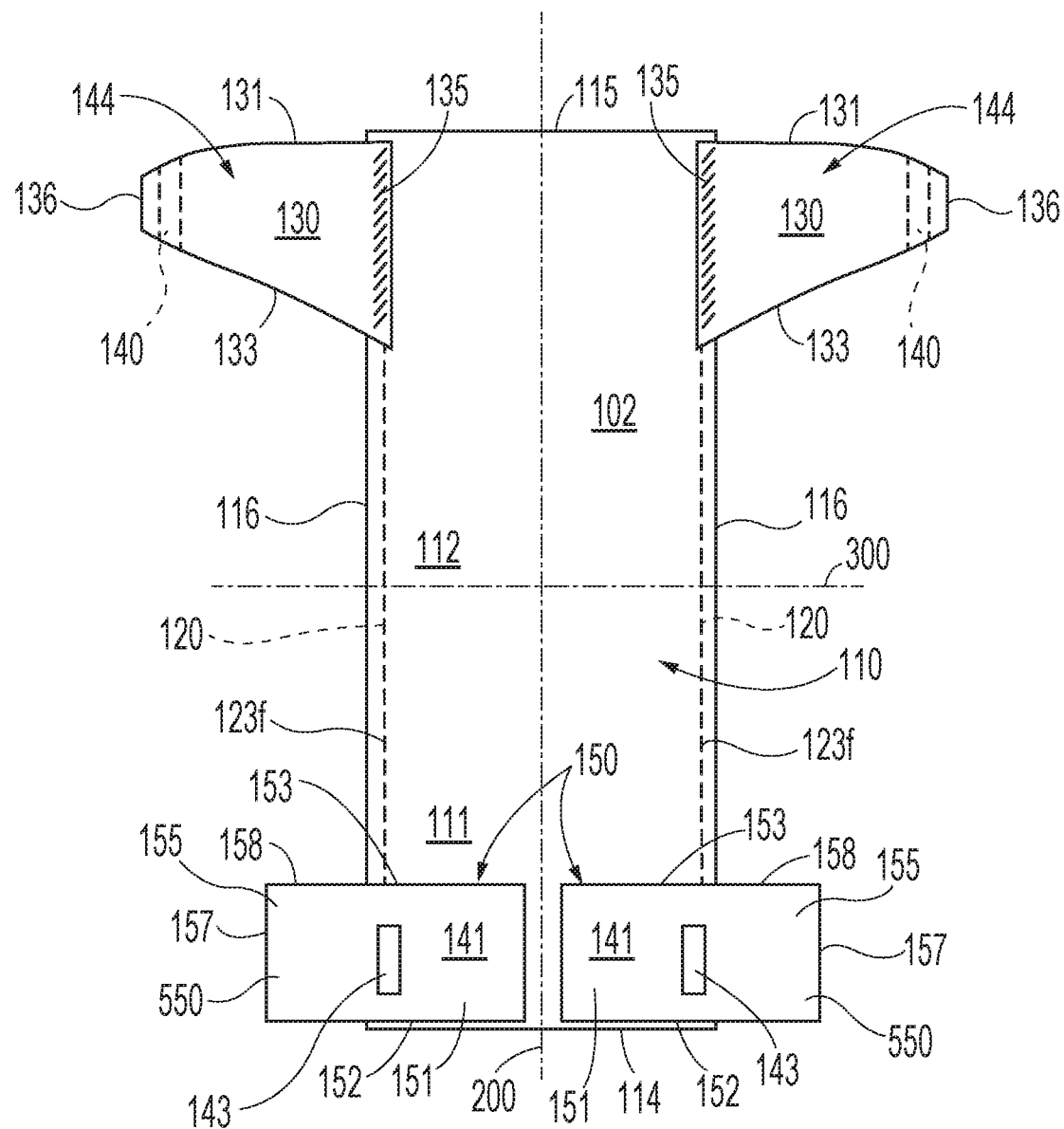
FIG. 3 is a schematic plan view of another example of diaper, outward-facing surfaces facing the viewer.
Figure 4:
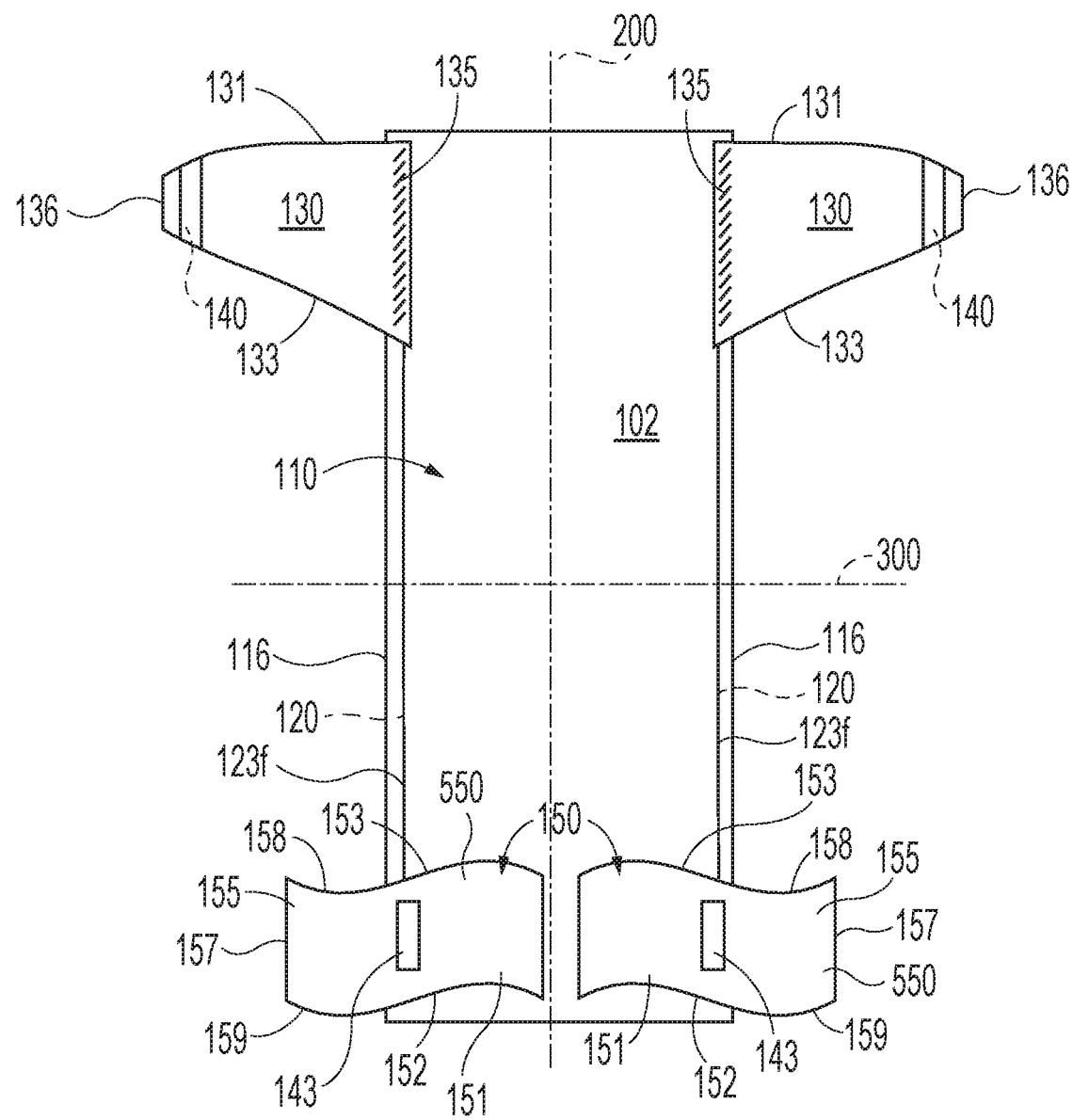
FIG. 4 is a schematic plan view of another example of diaper, outward-facing surfaces facing the viewer.
Figure 6:
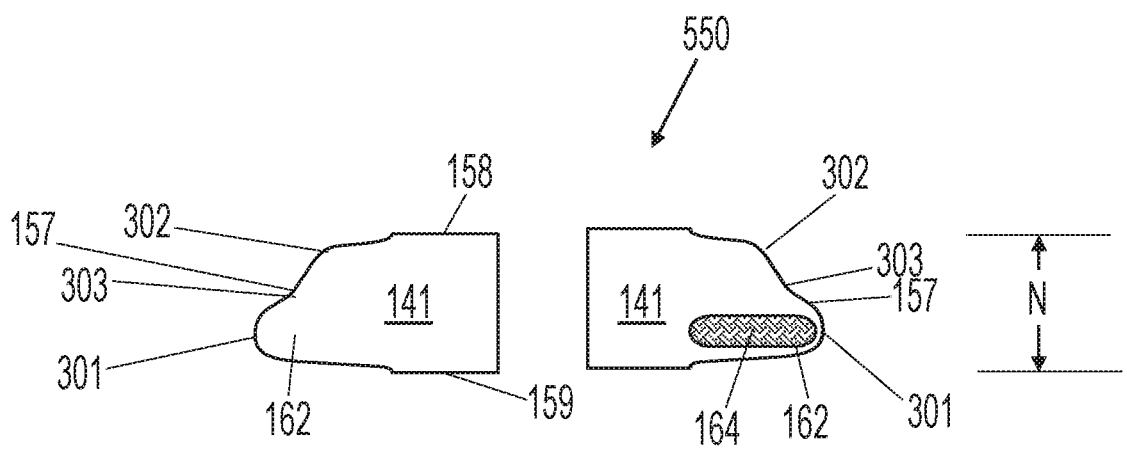
FIG. 6 is a schematic plan view of another exemplary combination belt structure.

Referring to FIGS. 3-4 and 6, in some examples, two discrete sections of web material 151 may be provided to provide respective left and right front ears 155 and provide or support respective left and right primary second components 141. In some circumstances, this configuration may simplify and/or reduce costs of manufacturing. For the avoidance of doubt, the discrete sections comprise a combination belt structure 550 as they each provide both support for a primary second component 141 and form an ear 155.

Referring to FIG. 4, in some examples, the inboard and/or outboard lateral edges 153, 152 of the section(s) of web material 151 may be curved rather than straight. In the example depicted in FIG. 4, the inboard lateral edge 158 in the front ear portion 155 has a concave curvature laterally outboard of the chassis. Such a curvature may provide for a comfortable and/or visually attractive fit of the diaper about the wearer, at the hip areas. Such a curvature may be accompanied by a curvature of the outboard lateral edges 159 having a profile that is parallel to that of the inboard lateral edge 158, which allows for nesting of shapes for the section(s) of web material 151 during manufacturing, enabling maximum usage of the web material component and/or minimization of waste.

In further nonlimiting examples, it may be desired that the inboard lateral edges 158 of front ears 155 extend downward toward the lateral axis of the diaper, outboard of the longitudinal edges 116 of the chassis. This may be desired in some circumstances to provide greater coverage of the wearer's skin at the hip areas, or to provide greater assurance that a portion of the section of web material 151 forming the front ears is present to protect the wearer's skin from possible contact with a fastening component.

Figure 5:
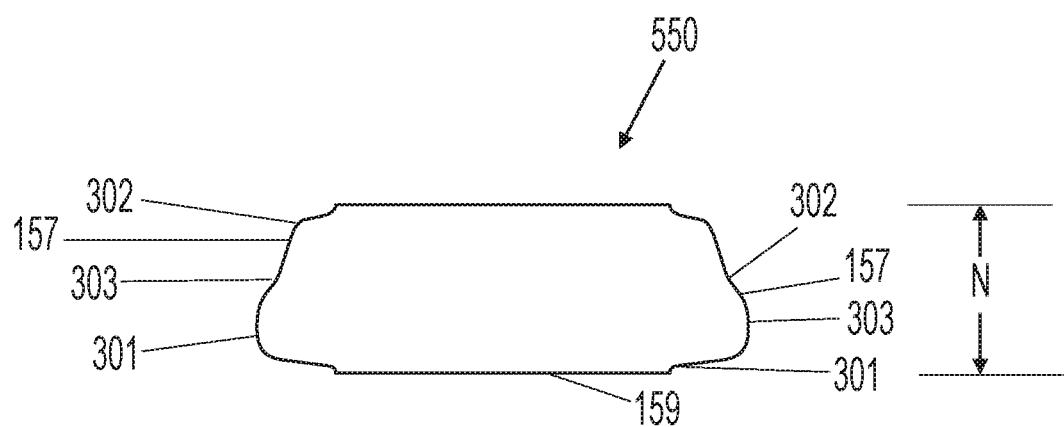
FIG. 5 is a schematic plan view of an exemplary combination belt structure.

Further to the above, a front ear 155 may be configured to fit about the upper thighs and hip region of the wearer. When the ear is provided as a portion of a combination belt structure 550, the belt 550 may be adapted to be fit the complex geometry that includes both the front waist area and at least a portion of the hip and upper thigh regions of the wearer. As shown in FIGS. 4 and 5 for example, the belt may have a varying width throughout at least a portion of its longitudinal length. As illustrated in FIGS. 5 and 6, a longitudinal edge 157 may comprise a curvilinear shape. The curvilinear shape may have at least two convexities 301 and 302 and at least one concavity 303 disposed intermediate the two convexities. The convexities may be disposed at different lateral positions, such that one is more laterally inboard relative to the other. In some embodiments, one convexity 301 may be disposed both laterally outboard and longitudinally outboard of the other convexity 302. In embodiments where the article (or belt) comprises two ears disposed on opposite lateral sides, each ear may comprise two convexities with one concavity therebetween. In such embodiments, the lateral distance between longitudinally outboard convexities 301 may be greater than the lateral distance between the two longitudinally inboard convexities 302 (see FIG. 2). Without wishing to be bound by theory, it is believed these embodiments allow the belt to fit smoothly into the body's complex geometry and provides a more comfortable wearing experience by allowing the wearer's legs to move with less hindrance from material (i.e., the belt is narrower near the upper thighs) while maintaining a secure fit around the waist. In addition, minimizing the amount of material proximate to the inboard edge reduces the likelihood of the material folding over when positioned beneath the base member during application, and thereby increases fit and comfort.

Referring to FIG. 6, the ear 155 may comprise a grip portion 162. The grip portion 162 is an area of the ear that may be used to pull the front ear flat while wrapping the rear waist region about the wearer to fasten. In certain embodiments, the grip portion is located closer to the outboard lateral edge 159 of the ear than the inboard lateral edge 158. The ear may be configured to identify the grip portion. In nonlimiting examples, the ear (or combination belt structure comprising the ear) comprises its largest width at a convexity 301 as shown in FIGS. 5-6. Without being bound by theory, it is believed that such configuration intuitively indicates an area suitable for a thumb and/or finger grip as shown in FIG. 6. Additionally, or alternatively, the grip portion 162 may be provided with a signal 164 to distinguish the area from the remaining ear. The signal may comprise a color, a texture, pattern (e.g., bond pattern), and/or indicia (e.g., words, logos, trademarks).

Figure 7A:
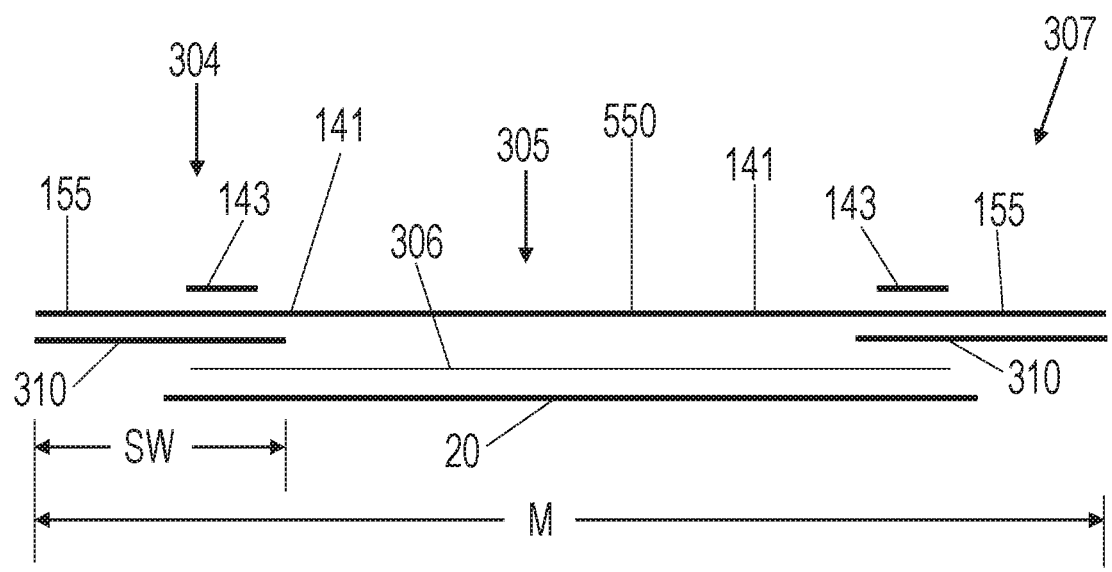
FIGS. 7A-7B are schematic cross-sectional views taken along line 7-7 in FIG. 1A according to nonlimiting embodiments.
Figure 7B:
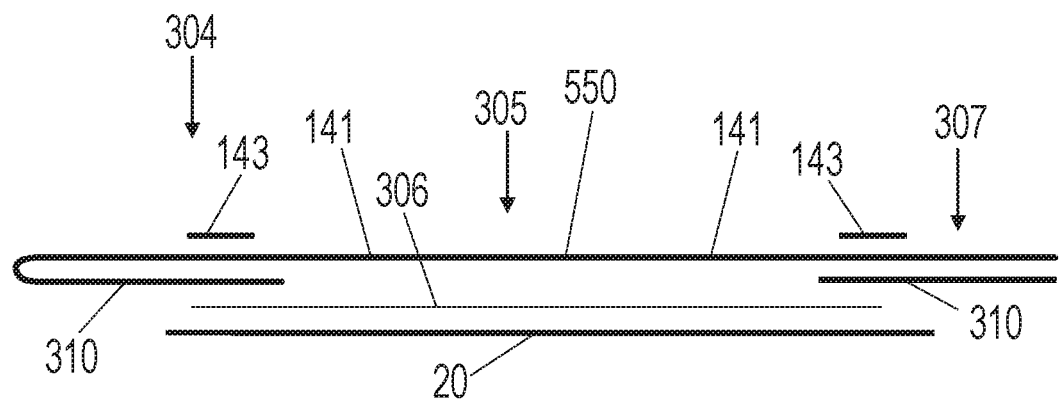

Additionally, or alternatively, the front waist region may comprise a variation in stiffness. The stiffness of the front waist region may vary in the lateral direction. Turning to FIGS. 7A-7B, in certain embodiments, the front waist region comprises a bending resistant zone 304, which is at least partially disposed outboard of the longitudinal edge 116. The bending resistant zone 304 may comprise a Stiffness of at least about 0.2 N/mm, or at least about 0.6 N/mm up to about 1 N/mm, or up to about 0.96 N/mm, or from about 0.2 N/mm to about 1.5 N/mm, or from about 0.6 N/mm to about 1 N/mm reciting for said range each 0.1 N/mm increment therein, according to the Stiffness Test Method herein. The bending resistant zone may include a portion of the combination belt structure. In nonlimiting examples, the bending resistant zone includes at least a portion of a front ear 155. The bending resistant zone may be formed from the layers of the front ear (or layers of the combination belt structure comprising the front ear). One or more stiffening components 310, such as additional nonwoven layer(s), may also be used to form the bending resistant zone.

The stiffening component may provide more stiffness to an ear 155 and/or provide or support a primary second component 141. Additionally, or alternatively, the stiffening component may provide or support a secondary first component 143. The stiffening component 310 may comprise a separate layer of material as shown in FIG. 7A and/or a folded layer of material, such as a folded belt or ear, as shown in FIG. 7B. The stiffening component may comprise a nonwoven, a film, an adhesive and combinations thereof. Additionally, or alternatively, the stiffening component may comprise intermittent bonding to create a three-dimensional structure, such structure being more bending resistant than flat structures formed from continuous bonding. In nonlimiting examples, the stiffening component is disposed in overlapping relationship with the attachment means 306 of the combination belt structure—chassis composite. It is also contemplated that the stiffening element 310 be joined to the combination belt structure or to the chassis outside or separate from the area of attachment.

The stiffening component may have dimensions that correspond to the combination belt structure. Alternatively, the stiffening component may be different in shape or area than the combination belt structure. The stiffening component may comprise a maximum width, SW, of about 30 mm to about 350 mm, or from about 45 mm to about 300 mm, or from about 50 mm to about 250 mm, reciting for each range every 10 mm increment therein. In nonlimiting examples, the stiffening component may comprise a maximum width, SW, that is less than the maximum width, M, of the combination belt structure as shown for example in FIG. 7A. In this way, less material may be utilized, and the stiffening component may be positioned only where enhanced stiffness is desired. In other nonlimiting examples, the stiffening component comprise a maximum width, SW, that is greater than or equal to the maximum width, M, of the combination belt structure. In further nonlimiting examples, the stiffening component may extend laterally outboard of a longitudinal edge 157 of the combination belt structure. In such examples, the stiffening component may serve to provide additional coverage of the wearer's skin in the hip region and/or allows for the use of different nonwovens (e.g., softer nonwovens) against the wearer's skin.

Returning to FIG. 1A, the stiffening component may comprise a maximum length, SL. The combination belt structure may comprise a maximum length, O, in the area of overlap between the stiffener and combination belt structure. The stiffener maximum length, SL, may be substantially equal to the maximum length of the combination belt structure in the overlap area, O, as shown in FIG. 1A, for example. Alternatively, the maximum length of the stiffening component, SL, may be greater than or less than the maximum length of the belt structure in the overlap area, O. In further nonlimiting examples, the stiffening component may extend laterally outboard of a lateral edge 152, 153 of the combination belt structure. In such nonlimiting examples, the stiffening component may provide additional material around a fastening component, and thereby prevent exposure of the component (e.g., hooks) to the wearer's skin.

In further nonlimiting examples, an article comprises a first bending resistant zone 304 and a second bending resistant zone 307, which may be disposed proximate to opposite longitudinal edges 116, as shown in FIGS. 7A and 7B. The second bending resistant zone may include a portion of the combination belt structure, such as at least a portion of a front ear, and is at least partially disposed outboard of the longitudinal edge 116. The second bending resistant zone may comprise the same magnitude of stiffness as the first bending zone or the two zones may differ in stiffness.

Additionally, or alternatively, a bending resistant zone 304, 307 may vary in the magnitude of stiffness from a reference zone 305 by at least about 10%, or at least about 15%, or at least about 20%, or from about 10% to about 50% as determined by the Stiffness Test Method herein, reciting for said range every 5% increment therein. The reference zone 305 is disposed entirely inboard of the longitudinal edges 116. The reference zone may at least partially include a portion of the combination belt structure.

In some embodiments, the rear waist region comprises variations in stiffness as described herein with respect to the front waist region.

To supplement the primary fastening system, the article may include a secondary fastening system 142, as is shown in FIG. 1C for example. The secondary fastening system may comprise a secondary first component 143 and a secondary second component 144. In nonlimiting examples, the diaper may include a pair of secondary first components 143 disposed on an outward-facing surface of the front waist region and a pair of secondary second components 144 disposed on a wearer-facing surface of the rear waist region. The secondary first components 143 may be any suitable fastening component configured to fastenably engage with the secondary second components 144, and vice versa. The secondary fastening first and second components may have any of the features noted above with respect to the primary first and second components respectively. The secondary fastening system may comprise any of the nonlimiting examples of engageable fastening components referenced above. In a particular example, secondary first components 143 may be patches of hooks, and material disposed on or forming the outward-facing sides of the base member may be, or include, material that serves as the loops component of a hook-and-loop fastening system. In nonlimiting examples, a wearer-facing layer forming the base member 130 may include a nonwoven material adapted to serve as a secondary second component 144 and fastenably engage with hooks constituting the secondary first components 143. The secondary second component 144 may be formed from extensible material or substantially non-extensible material. As described above with respect to the primary first component, the secondary first component may be a separate patch of material joined to the web material or may be integrally formed from the web material by process described above.

Figure 2:
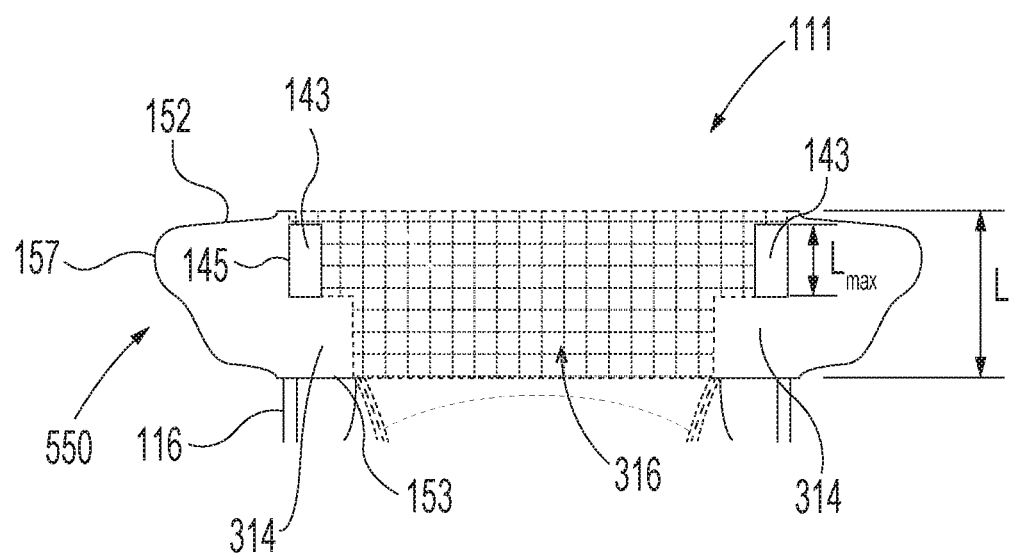
FIG. 2 is a schematic plan view of an example of a front waist region with layer(s) removed to reveal a nonlimiting example of anchoring zone.
Figure 2A:
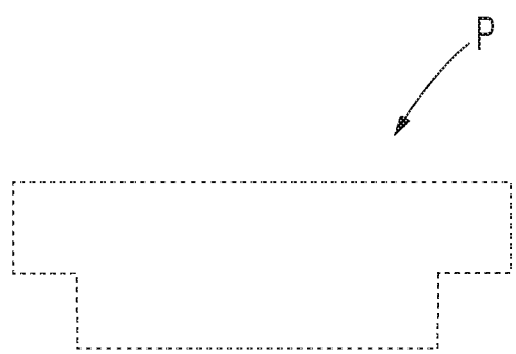
FIG. 2A is a schematic depiction of an exemplary perimeter of an anchoring zone in FIG. 2.

Turning to FIG. 2, in embodiments comprising a decoupled zone 314 and an anchoring zone 316, the secondary first component may be at least partially disposed within the perimeter P of the anchoring zone.

In further nonlimiting examples, the web material comprising the secondary first component (e.g., hooks) may also comprise the primary second component (e.g., loops). Additionally, or alternatively, the polymeric material comprising the primary first component (e.g., hooks) may also comprise the secondary second component (e.g., loops). In such nonlimiting examples, said substrates (i.e., the web material, the polymeric material) may comprise a first constraint, where in any identifiable linear path along the section of material that
(a) has a width greater than 2 mm; and
(b) forms an angle of 45 degrees or less with the machine direction, in x-y plane along a major surface of the section of material,
at least partially overlies a bond or bonds in the pattern at a plurality of locations along the path. Further, the substrate may additionally comprise a second constraint, where the maximum identifiable dimension between locations at which bonds are overlaid by any such path is from 1 mm to 12 mm, more preferably from 2 mm to 10 mm, and even more preferably from 2 mm to 8 mm.

Further to the above, integral first components may be formed with varying directionality to provide different benefits in different sections of the component. For instance, hooks which are asymmetric about their vertical centerline (such that create an inverted J-shape or similar hook configuration) may be formed so that the open portion is pointed in the direction of expected engagement. In further nonlimiting examples, hooks in a front waist region may be imparted with directionality approaching or along the lateral direction and extending toward the longitudinal axis of the diaper. Such directionality provides mechanical structure extending in a direction opposite the ordinary direction of shear forces (directed away from the longitudinal axis in the front region) that would be exerted on the hooks in that region while the hooks are engaged during wear, providing for added fastening strength and/or more secure attachment, as compared with non-directional hooks of similar size, material utilization (shape volume) and numerical density. Hooks in the rear waist region may be imparted with directionality toward the longitudinal axis of the diaper (when the fastening member is in the open position). Such directionality would oppose the ordinary direction of shear forces that would be exerted on the hooks in the front waist region when the hooks are engaged (i.e., fastened) during wear, providing for added fastening strength and/or more secure attachment, as compared with non-directional hooks of similar size, material utilization (shape volume) and numerical density.

In certain embodiments, a fastening component may be longitudinally offset from a lateral edge of the component to which the fastening component is attached. As shown in FIG. 2 for example, a secondary second component 143 may be longitudinally offset from an outboard lateral edge 152 of the combination belt structure by at least about 1 mm, or at least about 3 mm, or at least about 5 mm, or from about 1 mm to about 20 mm, reciting for said range every 0.5 mm increment therein. In nonlimiting examples, a fastening component does not coincide with any lateral edge 152, 153 of the component to which it is attached. It may be desired, for example, that each secondary first component 143 is disposed with its surface area and outer edges entirely within the surface area and outer edges of the component (e.g., combination belt structure 550) to which it is joined.

The fastening component may have a maximum longitudinal length, $L_{max}$, that is equal to or less than the longitudinal length of the component to which the fastening component is attached. For example, the maximum longitudinal length, $L_{max}$, of the secondary second component may be less than the average longitudinal length of the component, L, in the area where the secondary second component is attached. $L_{max}$ may be about 95% or less, or 90% or less, or 85% or less, or from about 25% to about 95%, or from about 50% to about 90% of L, or from about 60% to about 85% or L, reciting for said range every 1% increment therein. Additionally, or alternatively, $L_{max}$ may be less than L by at least about 10 mm, at least about 15 mm, or from about 10 mm to about 50 mm, or from about 10 mm to about 30 mm, or from about 10 mm to about 15 mm, reciting for each range every 1 mm increment therein. Without being bound by theory, it is believed that offsetting the fastening component from a lateral edge prevents exposing the fastening component to a wearer's skin. Tension on areas of the article may result in folding or collapsing of materials surrounding the fastening component. By positioning the fastening component away from an edge, folding and collapsing is less likely to result in exposing the fastening elements to the skin. In other words, the material would be required to deform more before such exposure could occur.

Additionally, or alternatively, a fastening component may be laterally offset from a longitudinal edge of a component to which it is attached. For instance, an outboard longitudinal edge 145 of a secondary first component 143 may be laterally inboard of a longitudinal edge of an ear 157 by at least about 1 mm, or at least about 3 mm, or at least about 5 mm, or from about 1 mm to about 10 mm, reciting for said range every 0.5 mm increment therein. In nonlimiting examples, the outboard edge 145 of the secondary second component may be laterally inboard of a longitudinal edge 116.

It may be desired to cut or otherwise impart at least the lower edges of secondary first components 143 with rounded profiles or profiles other than 90 degree corners, rather than sharp corners as in a rectangular shape as depicted in the figures. This may be deemed desirable for purposes of reducing chances of chafing of the wearer's skin that might otherwise occur, through localized concentrations of pressure against the wearer's skin at sharp corners of components 143. Thus, it may be desired that, for example, patches of hooks material constituting secondary first components 143 have a circular, oval, elliptical, rounded rectangle or other shape lacking sharp corners, at least on the edges of the lower half of the length thereof.

Positioning of Fastening Components

Addition of a secondary fastening system can provide a greater surface area for fastening, and thereby de-concentrate lateral tensile forces communicated through the fastening location(s) as the rear waist region is pulled toward the front waist region, and vice versa, when the diaper is worn. In addition, having two distinct fastening locations reduces the tendency of the front portion of the article to pivot (i.e., pivot around the single fastening location of the primary fastening system). Further, the secondary system helps to create a line of tension closer to the front waist edge, which may reduce the likelihood of folding or flipping over of the front waist edge during wear. Further still, the secondary system may create an anchoring geodesic to direct forces from the crotch region to over the hips in order to prevent sagging during wearer. The secondary system may also help to secure the front ear or combination belt structures in place during wear. Each of the foregoing can serve to provide for more effective and durable fastening and less longitudinal and/or lateral flexing, sagging and/or wrinkling of the diaper materials about the fastening areas during wear. To most effectively provide these benefits, particular locations for the fastening components, relative the other features of the diaper, may be desired.

Figure 8:
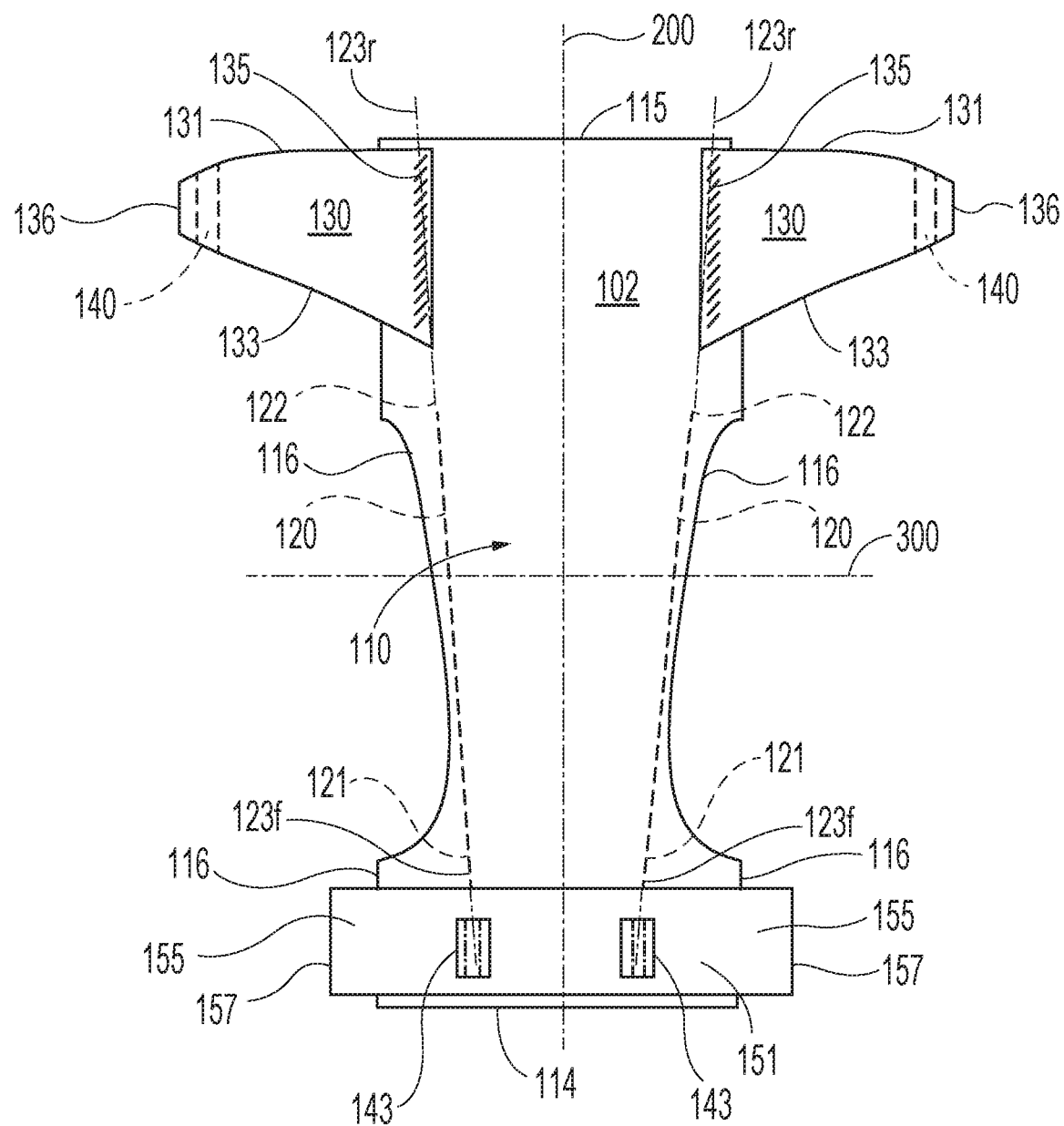
FIG. 8 is a schematic plan view of another example of diaper, outward-facing surfaces facing the viewer.
Figure 9:
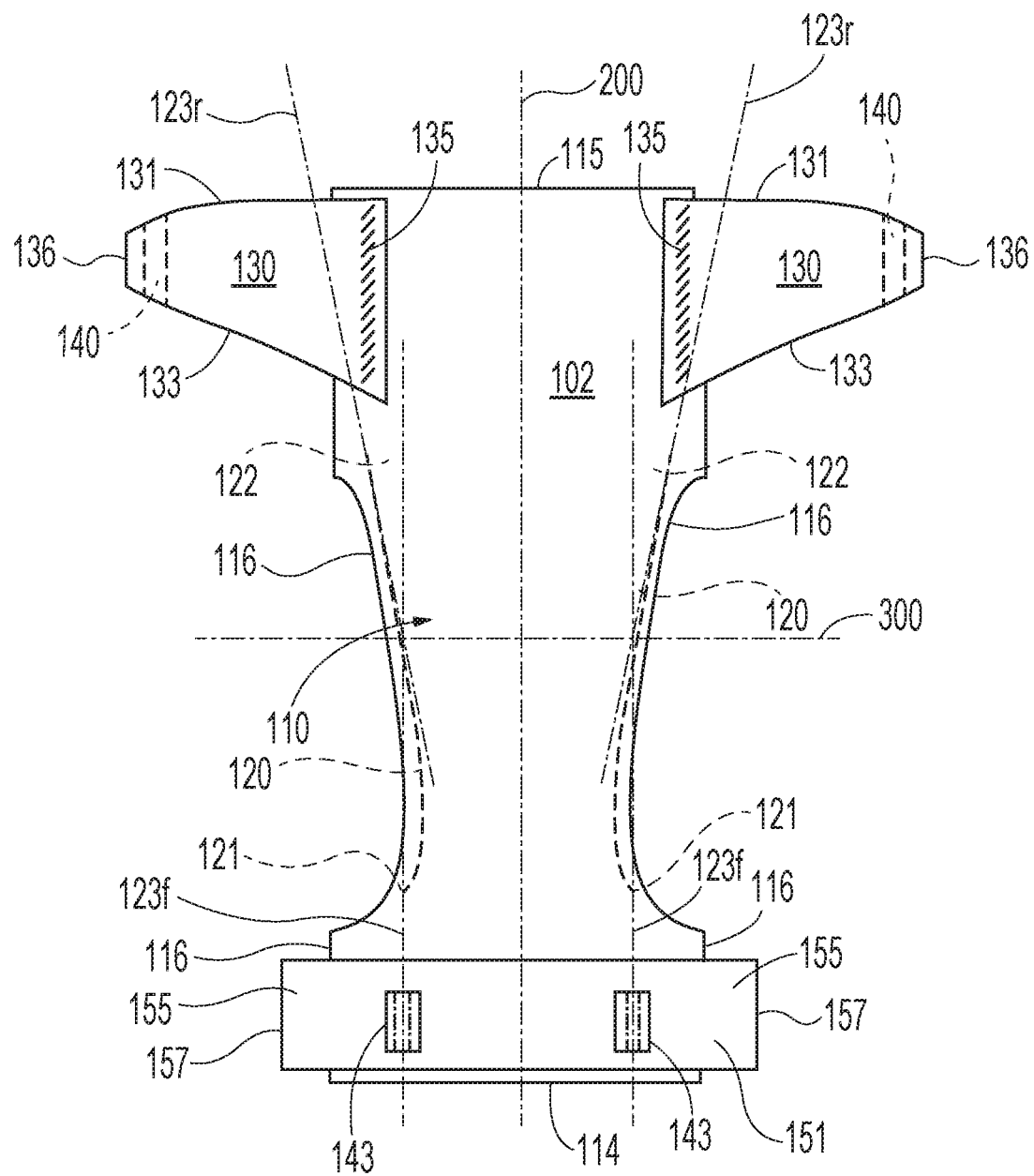
FIG. 9 is a schematic plan view of another example of diaper, outward-facing surfaces facing the viewer.

Turning to FIG. 8, the article 10 may include leg band elastic members 120. Each band elastic member 120 may have an active portion extending between a front end 121 and a rear end 122 thereof, in which the elastic member is pre-strained and thereby effects longitudinal contraction and gathering of materials along the proximate longitudinal edge 116. In some examples, the leg band elastic members 120 may have inactive portions extending beyond the front and rear ends 121 and 122, where they are not pre-strained, or have been deactivated in some manner. The leg band elastic members 120 will lie along or intersect front leg band lines 123f. Referring to FIG. 9, where a leg band elastic member 120 is curved, its associated front leg band line 123f is the line that connects the point of intersection of the leg band elastic member 120 with the lateral axis 300, and the front end 121 of the active portion of the elastic member 120. It will be appreciated that the front leg band line 123f and the elastic member 120 are collinear when the active portion of the elastic member 120 is straight. For purposes herein, a leg band line lies along the most laterally outboard leg band elastic member (where, for example, more than one leg band elastic member is present along a longitudinal edge 116), and the most laterally outboard edge thereof.

Figure 10:
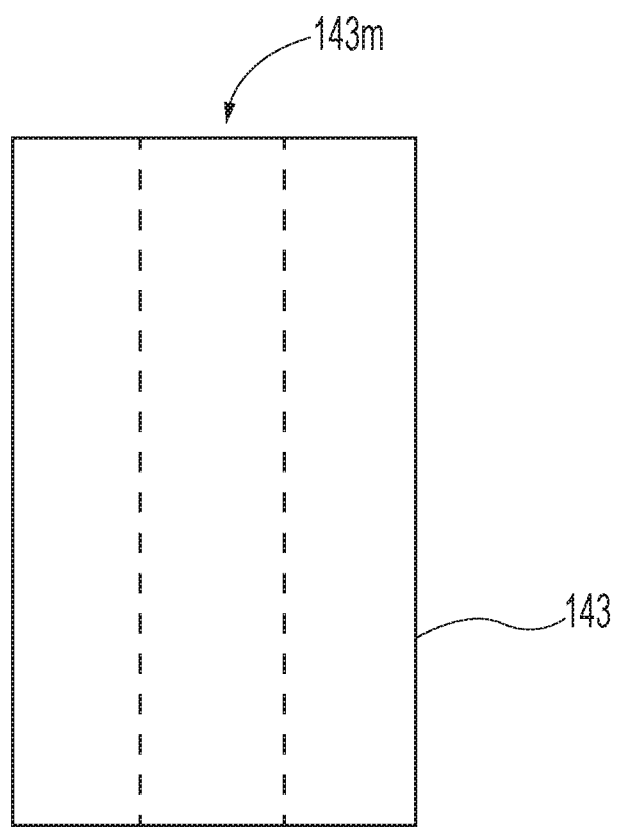
FIG. 10 is an enlarged schematic plan view of an example of a fastening component.

For purposes of most effectively providing the benefits noted above, it may be desired that the secondary first component 143 be located along the lateral direction such that it lies tangent to, or along, the front leg band line 123f. Such a location places the secondary first component along the line of generally longitudinal tension created by the leg band elastic member, providing desirably located support and thereby helping to prevent twisting or skewing of the front waist region of the diaper about the primary first component when the diaper is fastened about a wearer. For these purposes, it may be even more particularly desired that the middle third of the width 143m of the secondary first component 143 (see FIGS. 8-10) be located such that it lies tangent to, or along, the front leg band line 123f.

Still referring to FIGS. 8 and 9, base members 130 that are formed of sections of materials that are discrete from those of the chassis may be bonded to the chassis by chassis attachment bonds 135. Chassis attachment bonds 135 may each be a single bond, or a series of bonds, with its longer dimension generally aligned in the longitudinal direction. It may be desired the chassis attachment bond 135 be tangent to, or along, the rear leg band line 123r. Such a location places the bond 135 (which is generally, relatively stiff) along the line of generally longitudinal tension created by the leg band elastic member 120, providing desirably located structural stiffness and resulting support and thereby helping to prevent twisting or skewing of the rear waist region of the diaper about the bond when the diaper is fastened about a wearer. Referring to FIG. 9, where a leg band elastic member 120 is curved, its associated rear leg band line 123r is the line that connects the intersection of the leg band elastic member 120 with the lateral axis 300, and the rear end 122 of the active portion of the elastic member 120. It will be appreciated that the rear leg band line 123r and the elastic member 120 are collinear when the active portion of the elastic member 120 is straight.

To maximize the likelihood that the secondary first component 143 will be covered, and otherwise will be unlikely to come into undesirable contact with the wearer's skin during wear, it may be desired to locate the secondary first component 143 in a suitable location along the longitudinal direction relative to the other portions of the diaper. Returning to FIG. 1A, each base member 130 has a top edge 131 and a bottom edge 133. Top edge 131 meets longitudinal edge 116 of the chassis at upper intersection point 132. Bottom edge 133 meets longitudinal edge 116 of the chassis at lower intersection point 134. Lower intersection point 134 lies distance D2 from the rear waist edge 115. Upper intersection point 132 lies a distance D1 from the rear waist edge 115. When the fastening members 130 are integral extensions of one or more of the topsheet and backsheet as suggested in FIG. 1B, for purposes herein the upper intersection point 132 lies at the intersection of the rear waist edge 115 and a line perpendicular to the front waist edge and tangent to the longitudinal edge 116 where the diaper not including front ears 155 is widest forward of lateral axis 300, as illustrated in FIG. 1B. Similarly, the lower intersection point 134 lies at the intersection or meeting of the lower edge 133 with the line just described. The secondary first component 143 may be longitudinally located entirely between distances D1 and D2, from the front waist edge. When the fastening members are suitably shaped, such longitudinal location can help ensure that secondary first component 143 will be entirely covered by the base member when the diaper is fastened about a wearer for which the diaper is sized.

Referring again to FIG. 1A, an inboard intersection point 137 of the inboard lateral edge 153 of the web material 151 and the chassis may be located a distance D4 from the front waist edge 114. It may be desired that secondary first component 143 be located entirely outboard of the inboard lateral edge 153. It may further be desired that the secondary first component be located at a distance from the front waist edge 114 that is entirely less than distance D4 from the front waist edge 114. Such a location will help ensure that a portion of section of web material 151 is available to provide shielding and cushioning for the wearer's skin, against possible irritation that may be caused by the lower edges of secondary first component 143.

It may also be desired that secondary first component 143 be located closer to the outboard lateral edge 152 of the section of web material than to the inboard lateral edge 153 of the section of web material. This may be generally desired so as to locate the secondary first components as close the front waist edge 114 as practical, so as to help minimize or avoid flipping over of portions of the chassis proximate the front waist edge 114, when the diaper is worn.

As shown in FIG. 1A, the inward-most extent 139 of the primary first component 140 is located a distance D3 from the rear waist edge. It may be desired that distance D3 be less than distance D4. This will help ensure that a portion of the section of web material 151 is disposed below the primary first component 140 when the diaper is fastened and worn, thereby providing shielding and cushioning for the wearer's skin, against possible irritation that may be caused by the lower edges of primary first component 140. This may be particularly desirable in a situation in which a caregiver desires to fit the diaper as loosely on the wearer as possible, by, e.g., affixing the primary first component 140 to the front ear, laterally outboard of the longitudinal edge of the chassis rather than at a more laterally inward location on the front waist region/landing zone 150.

For purposes of avoiding flipping or roping of the base member 130 about a line of lateral tension that would otherwise be localized about a primary first component 140 when the diaper is fastened, the secondary first component 143 may have a longitudinal length that is greater than the length of a primary first component 140. In other circumstances, however, it may be desired that the length of a secondary first component 143 be less than that of a primary first component 140, which may help reduce chances of irritation or chafing of the wearer's skin proximate edges of secondary first components 143 due to localized concentration of pressure proximate to such edges.

Folded Configurations

Figure 11:
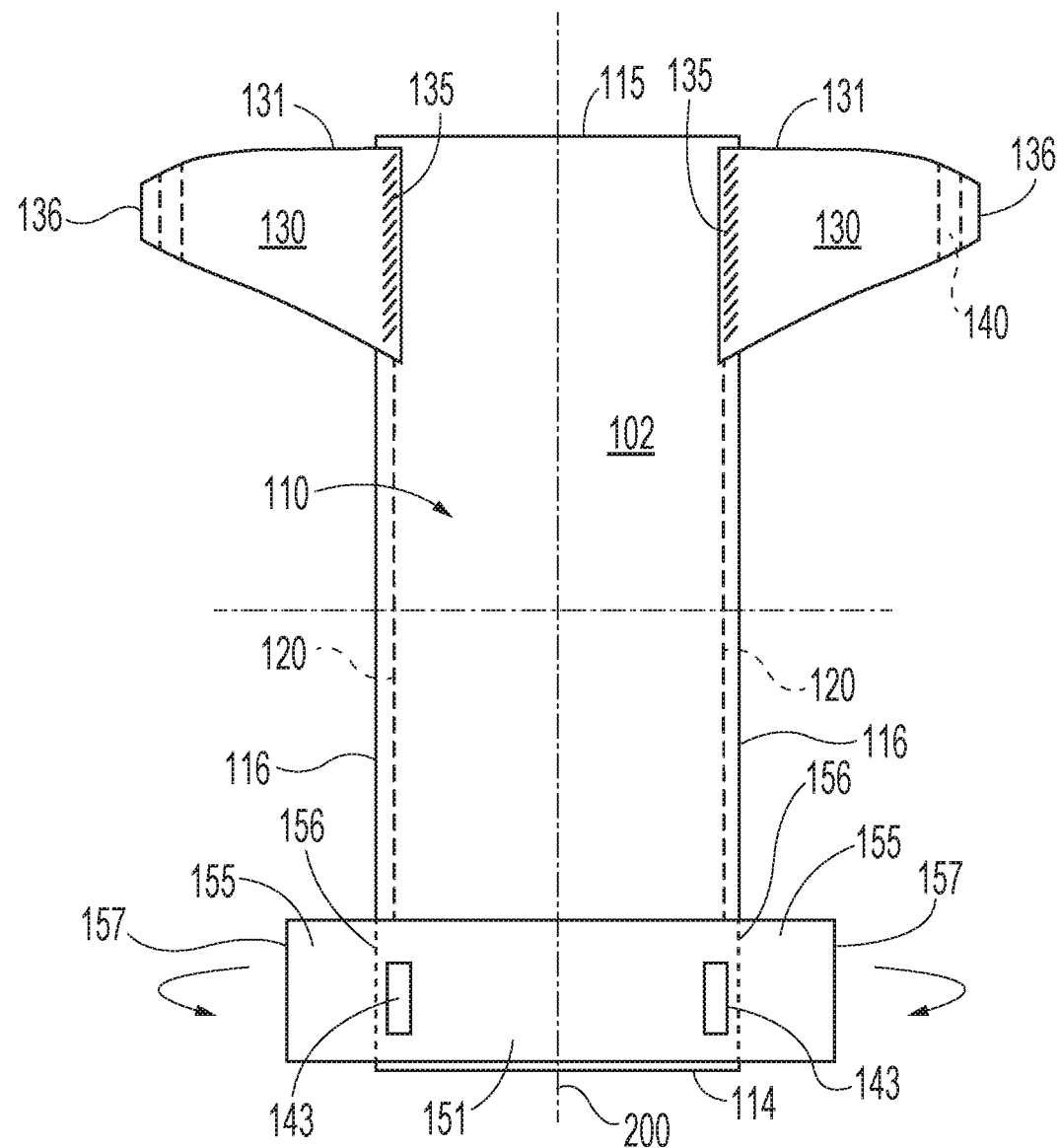
FIG. 11 is a schematic plan view of another example of diaper, outward-facing surfaces facing the viewer.
Figure 12:
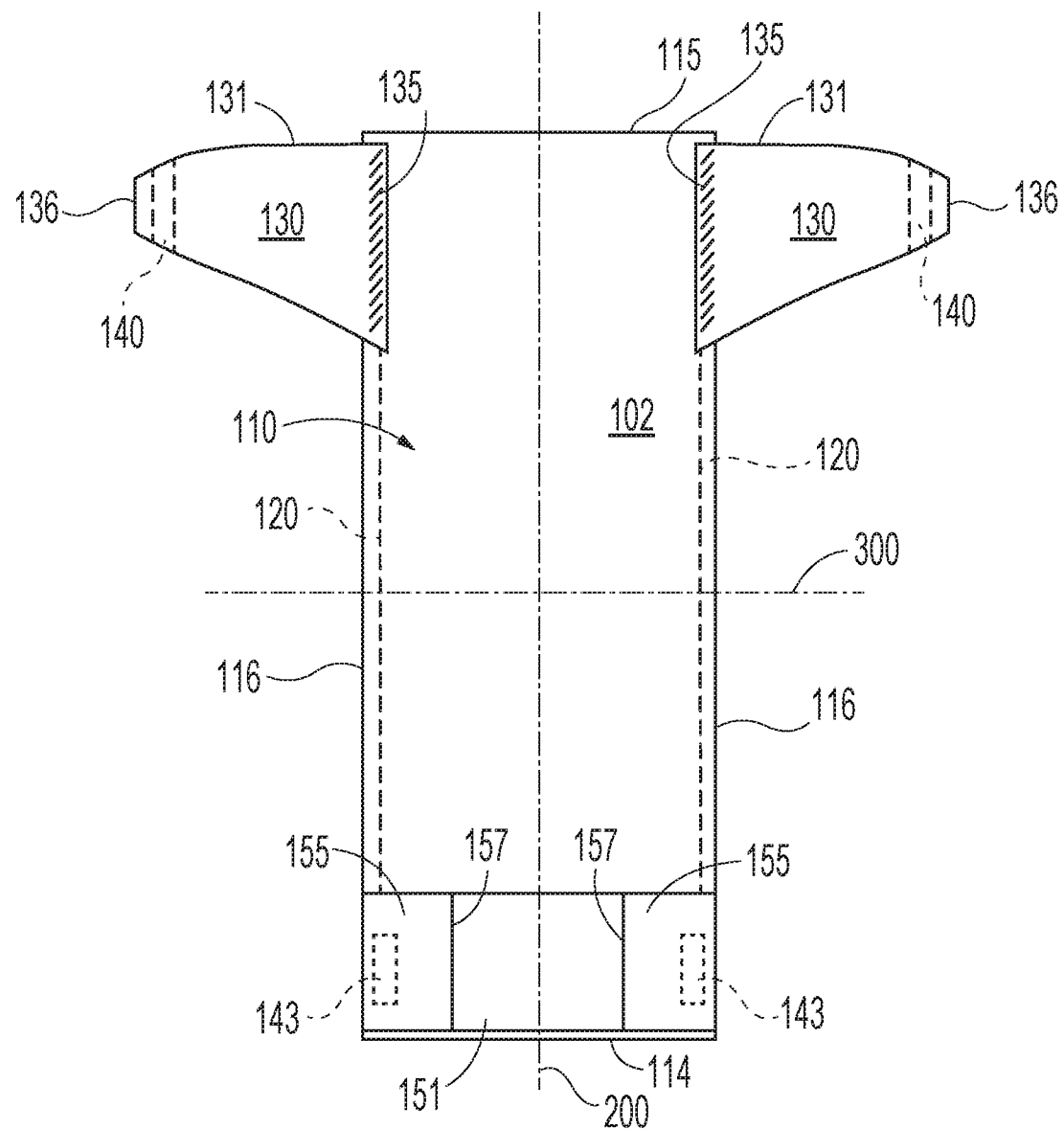
FIG. 12 is a schematic plan view of the diaper of FIG. 11, outward-facing surfaces facing the viewer, shown with front ears folded over laterally.
Figure 13:
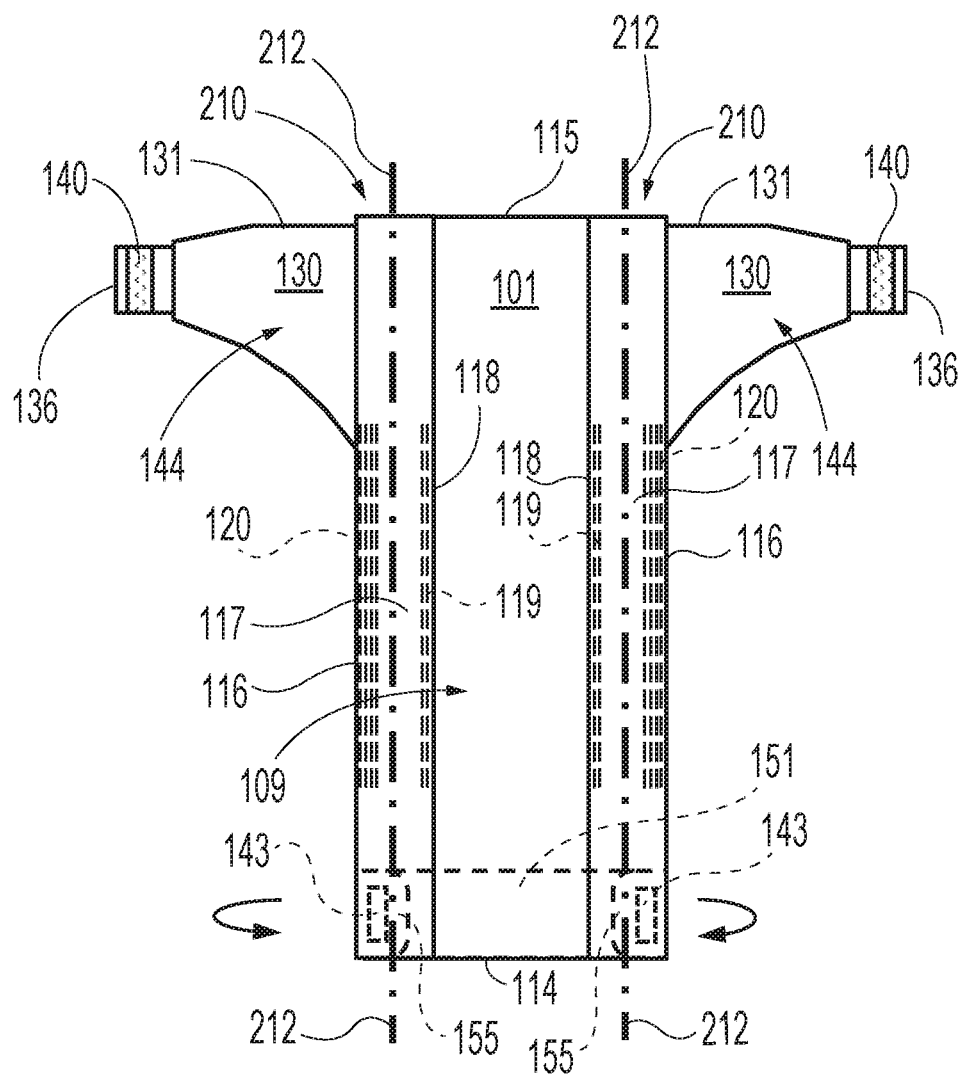
FIG. 13 is a schematic plan view of another example of a diaper, wearer-facing surfaces facing the viewer, shown with front ears folded over laterally.
Figure 14:
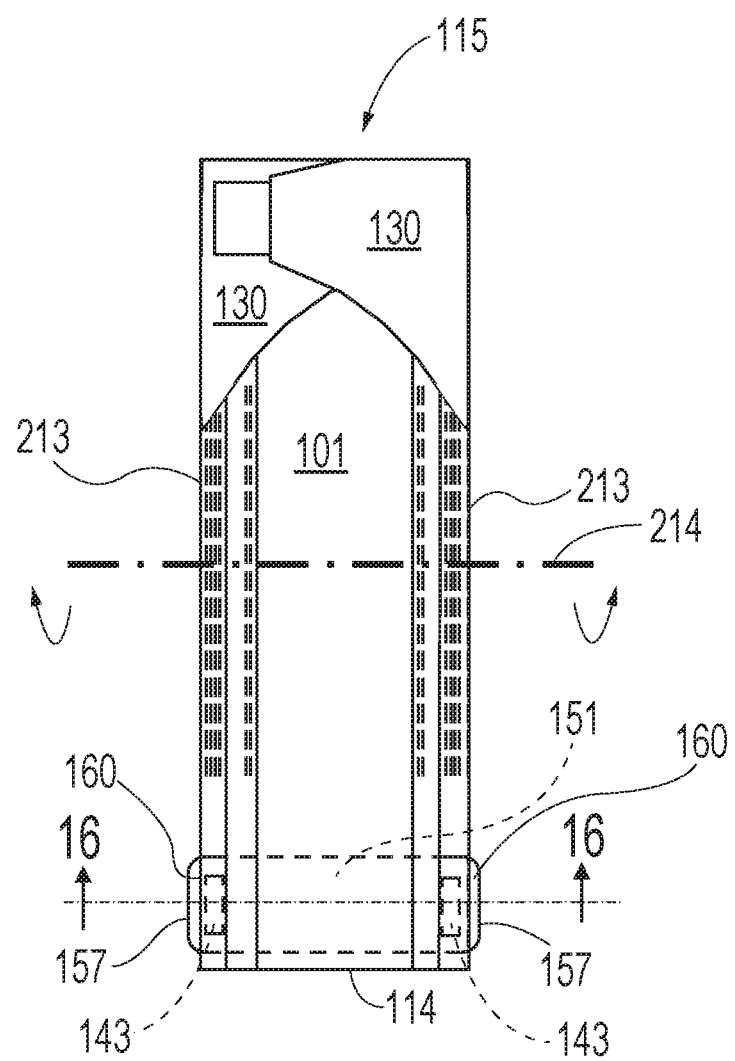
FIG. 14 is a schematic plan view of the diaper of FIG. 13, wearer-facing surfaces facing the viewer, shown with fastening members and side margins folded over laterally.
Figure 15:
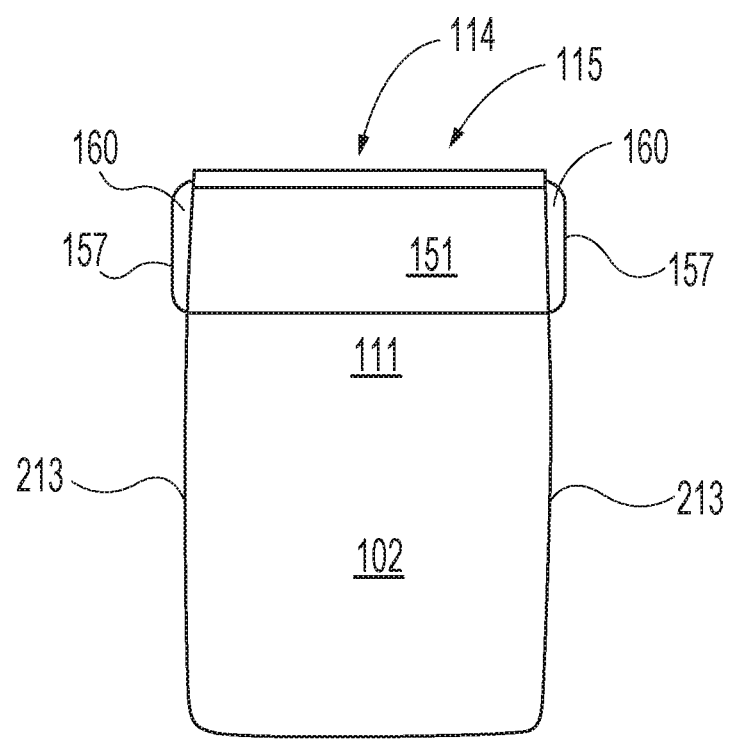
FIG. 15 is a schematic plan view of the diaper of FIG. 14, shown folded approximately in half about a lateral fold line with wearer-facing surfaces in and outward-facing surfaces out.
Figure 16:
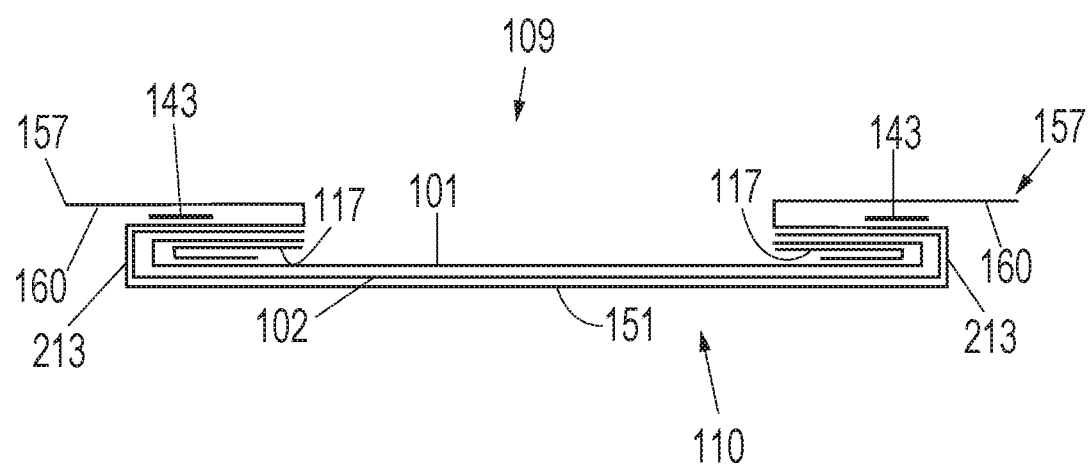
FIG. 16 is a schematic lateral cross section of the diaper of FIG. 14, taken through line 16-16 in FIG. 14.
Figure 17A:
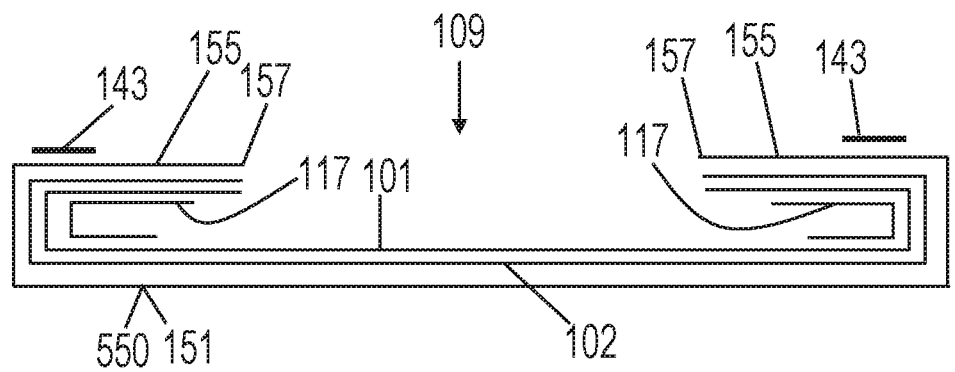
FIG. 17A is a schematic lateral cross section of a front waist region in nonlimiting example of another folded configuration.
Figure 17B:
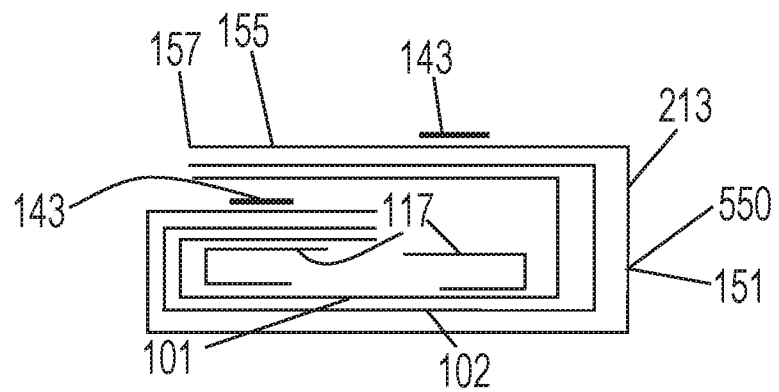
FIG. 17B is a schematic lateral cross section view of a front waist region in a nonlimiting example of another folded configuration.
Figure 17C:
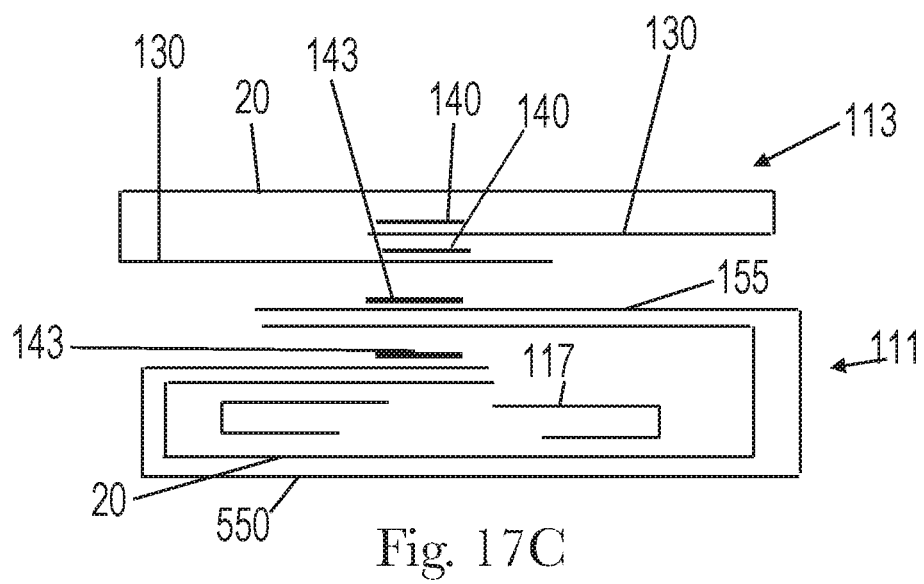
FIG. 17C is a schematic lateral cross section view of a diaper in a nonlimiting example of folded configuration.

Turning to FIGS. 11-17C, it may be desired to provide the absorbent article in a folded configuration, including folding the front ears. In certain embodiments, folding may serve to cover a fastening component which may be disposed on the chassis, combination belt structure or a combination thereof. By way of nonlimiting example, prior to or following the attachment of the section of web material 151 to the chassis, the front ears 155 may be folded laterally back over along longitudinal front ear fold lines 156, such that distal ends 157 of front ears 155 in such folded configuration are disposed laterally inboard of longitudinal edges 116 following attachment of the section of web material 151 to the chassis. As shown in FIGS. 11-12 for example, the front ear 155 may be folded toward the outward-facing surface 110 along the longitudinal front ear fold line 156. A portion of the combination belt structure 550 may then be folded inward along another fold line 212 as shown in FIG. 13, resulting in a z-fold configuration wherein the secondary first component is covered by the ear as shown in FIG. 16. In another configuration shown in FIGS. 17A-17C, the front ear 155 may be folded toward the wearer-facing surface 109, in an e-fold configuration. In some examples having a set of opposing front ears, at least one of secondary first component 143 may be covered the opposite ear in the folded configuration as shown in FIGS. 17B and 17C.

A folded front ear configuration may provide several advantages. First, it provides for control over the front ears 155 as the chassis moves through any further downstream processing, folding and/or packaging, reducing chances that front ears 155 will snag in any equipment, with possible resulting damage. Second, where secondary first components 143 of a secondary fastening system are included, folding the ears 155 over one or more secondary first components 143 will shield and protect the secondary first components from unwanted contact and interaction with other portions of the diaper prior to its use. For example, where secondary first components 143 are patches hooks material, it may be undesirable to have them exposed when, e.g., the entire diaper is folded for packaging as will be described below, because they may undesirably snag and/or undesirably attach to other portions of the diaper in such folded diaper configuration. In order to reduce chances of a negative caregiver perception of design and/or process quality, it may be desired that each fold line 156 be located no more than 10 percent of the front ear 155 width, from the proximate longitudinal edge 116.

Front ears 155 may be held in place in such folded ear configurations, for example, by releasable attachment to a secondary first component 143. A front ear may be held through pressure or friction. Alternatively, or in combination, each front ear 155 may be held in placed in such folded ear configuration by one or more releasable tack bonds bonding the section of web material 151 to itself. The releasable tack bonds may be adhesive bonds, thermal bonds or any other suitable bonding mechanism by which attachment between components is effected, but substantially non-destructive detachment thereof may be effected by gently tugging the front ear laterally outward. In one nonlimiting example, releasable tack bonds may be formed by a frangible bonding agent such as described in U.S. Pat. No. 8,454,571, disposed between the components to be attached to one another. Such a frangible bonding agent may have good adhesive strength when freshly deposited but may lose adhesive strength over time, thereby providing for good holding during manufacturing but providing for easy, non-destructive detachment at the time of consumer use. An example of a frangible bonding agent is PHO 3005 type fugitive hot-melt adhesive available from H.B. Fuller, St. Paul, Minn. In another non-limiting example, a frangible bonding agent may be a material forming a relatively weak bond (i.e., weaker than that formed by typical diaper construction adhesives) such as but not limited to a wax, for example, paraffin wax, microcrystalline wax, synthetic wax, beeswax and other natural waxes.

Regardless of any mechanism used to hold the front ears 155 in a folded ear configuration, however, it may be desired that a front ear 155 may be relatively easily peeled away from the surface from which the secondary first component is attached to facilitate unfolding without tearing or damage to the ear and/or said surface. In nonlimiting examples, the secondary first component may be peeled away by a peel force of about 2 N or less, or from about 0.2 N to about 2 N, or about 1 N to about 1.5 N, reciting for each range every 0.2 N therein. This peel force limit may be observed to reduce chances of caregiver difficulty and/or dissatisfaction with the diaper product, during deployment of the front ears 155 for application to a wearer. Peel force may be adjusted by techniques that will be apparent to those skilled in the art, e.g., selection and sizing of hook material to be used as secondary first components 143; selection of web material to be used as section of web material 151; selection of adhesive to be used to form releasable tack bonds, size and/or pattern of releasable tack bonds, etc.

It is generally desirable that diapers of the type contemplated herein be folded to a more compact configuration for efficient packaging and shipping. Accordingly, in a first step, left and right side margins 210 of the diaper may be folded laterally inwardly, about left and right longitudinal diaper folding lines 212 as indicated by the curving arrows in FIG. 13, to bring the diaper to a first interim folded configuration depicted in FIG. 14, with left and right longitudinal folded edges 213. Referring to FIGS. 14 and 15, in a next step, the diaper may be folded over on itself and approximately in half lengthwise, wearer-facing surfaces in, about a lateral fold line 214, to bring it into a folded diaper configuration as shown in FIG. 15, which is a neat and compact configuration suitable for efficient stacking of a plurality of diapers, packaging and shipment. While FIGS. 13-15 illustrate ears that are folded toward the outward-facing surface, it is to be appreciated that the folding of side margins and lateral folding can be applicable when ears are folded toward the wearer-facing side. By way of nonlimiting example, FIGS. 17A-17C illustrate a folded article where the ears 155 are folded toward the wearing-facing surface 109 along with the article side margins 210. In such examples, the ears 155 are not folded toward the outward-facing surface prior to folding the side margins. The front ears may be folded as in FIG. 17A such that neither secondary first component is covered by an area of the front waist region. Alternatively, the front ears may be folded as shown in FIGS. 17B-17C, such that at least one secondary first component is covered by, and can be engaged with, an opposing front ear (i.e., the right secondary first component is covered by the left front ear or vice versa). Portions of the rear waist region may overlap with, and may be engageable with, secondary first components when the article is folded as is illustrated in FIG. 17C.

In certain embodiments, the section of web material 151, and the front ears 155, may be suitably sized, and the front ear fold lines 156 may be suitably located relative the chassis, such that the distal ends 157 of the front ears 155 are visible and easily identified and grasped by the caregiver when the diaper is in a folded diaper configuration. Referring again to FIG. 13 (depicting an example of a diaper with wearer-facing surfaces facing the viewer), front ears 155 are folded toward the outward-facing surface and are thereby located behind the diaper in the view shown. In FIG. 14, it can be seen that tab portions 160 and distal ends 157 of front ears are not folded about the folded edges 213, but rather, are left free to protrude laterally outboard of folded edges 213. In FIGS. 14-16, it can be seen that tab portions 160 of front ears 155 extend laterally away from the folded diaper in both the interim (FIG. 14) and final (FIG. 15) folded diaper configurations, and as such are readily visible and available to be grasped by the caregiver upon removal from the package and partial unfolding. The section of web material 151 forming the front ears 155 may be suitably sized, and longitudinal front ear fold lines 156 (see FIG. 11) may be suitably located, relative the chassis and longitudinal diaper fold lines 212 (see FIG. 13), to provide such laterally extending tab portions 160.

Components of the disposable absorbent article can at least partially be comprised of bio-sourced content as described in U.S. Pat. Pub. Nos. 2007/0219521A1, 2011/0139658A1, 2011/0139657A1, 2011/0152812A1, and 2011/0139659A1. These components include, but are not limited to, topsheets, backsheet films, backsheet nonwovens, side panels, leg gasketing systems, superabsorbent, acquisition layers, core wrap materials, adhesives, fastener systems, and land zones. In at least one embodiment, a disposable absorbent article component comprises a bio-based content value from about 10% to about 100%, or from about 25% to about 75%, or from about 50% to about 60% using ASTM D6866-10, method B. In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., WILEY® mill), and a representative sample of suitable mass taken from the randomly mixed particles.

Method of Forming Combination Belt Structures

Figure 18:
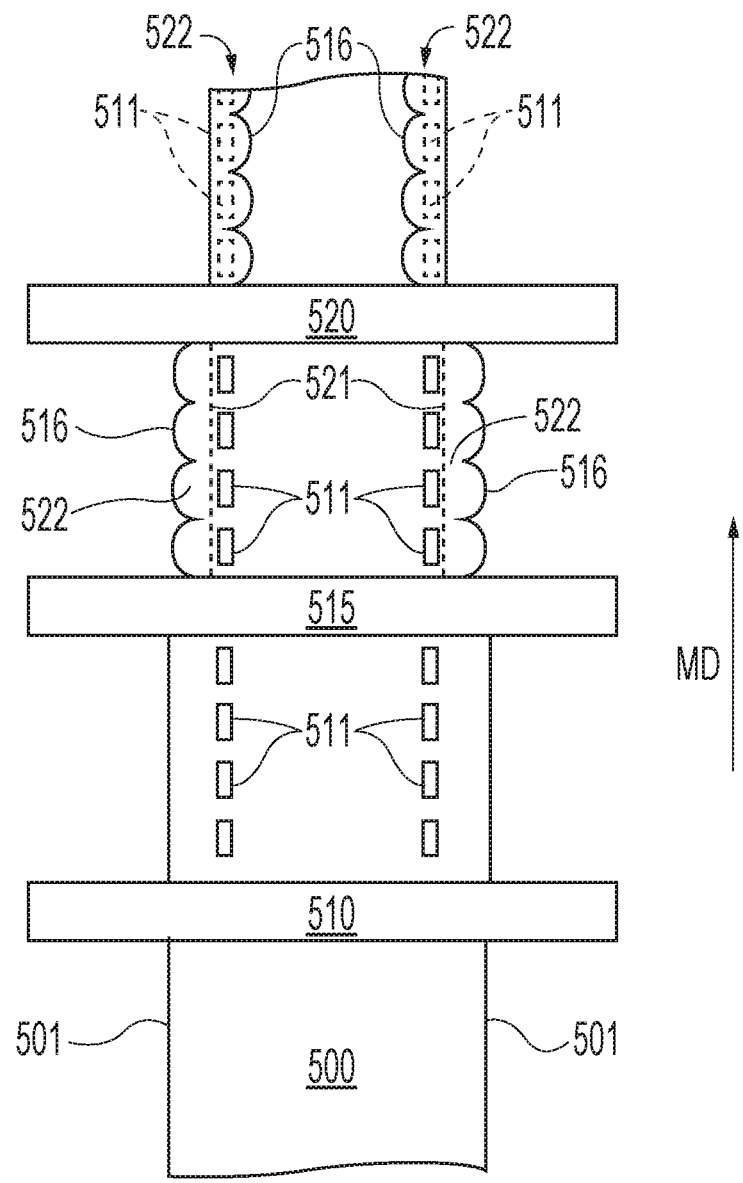
FIG. 18 is a schematic illustration of process steps for manufacturing belt structures.
Figure 19:
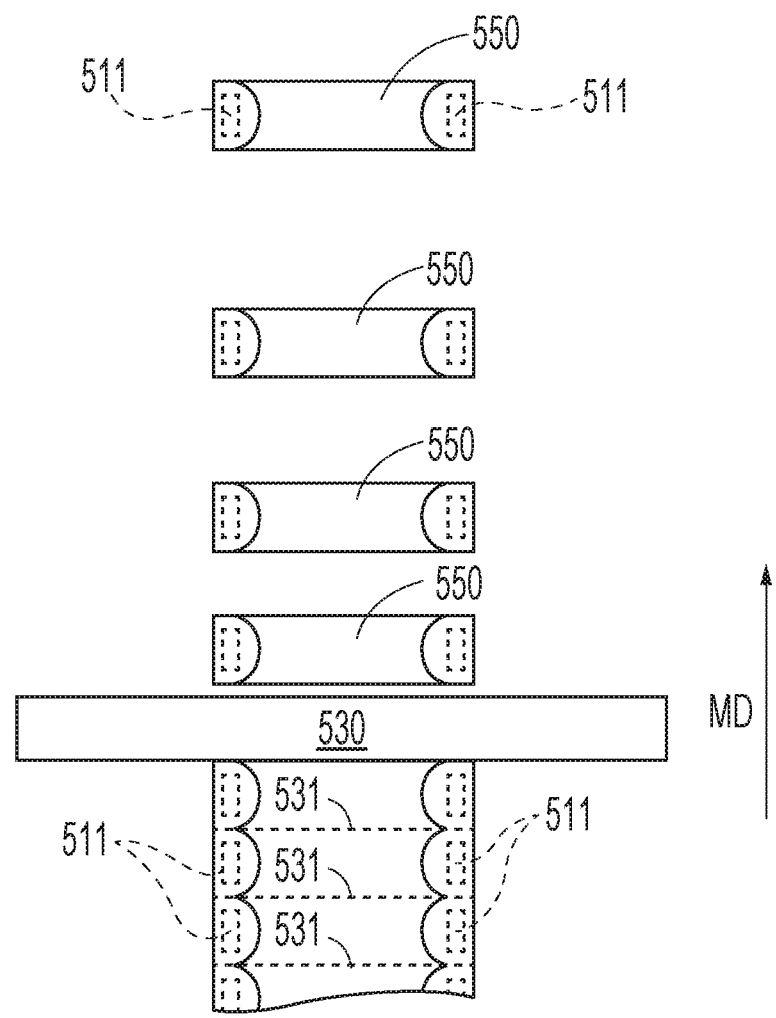
FIG. 19 is a schematic illustration of additional process steps for manufacturing belt structures.

Referring now to FIGS. 18 and 19, combination belt structures 550 may be manufactured from a strip of web material 500 having a cross direction width and side edges 501 along the machine direction. Web material 500 may be any web material suitable for serving as, or support, a primary second component of a primary fastening system and as material suitable for forming front ears. In some examples, web material 500 may be a nonwoven web material, adapted to receive and fastenably catch hooks included with primary first components, and thereby serve as the "loops" component of a hook-and-loop primary fastening system. In a more particular example, the section of nonwoven web material may be pattern bonded in a pattern of thermal bonds configured to enhance the strength and reliability of the material, and of the "loops" it provides. In a still more particular example, the section of nonwoven web material may be as described in any of the above-cited publications.

If, for example, a secondary fastening system is to be included with the diaper, strip of web material 500 may be conveyed along the machine direction MD to fastening component process equipment 510 configured to receive a supply of fastening components or fastening component material, and to affix fastening components 511 or fastening component material to the strip of web material 500. The fastening components may be registered with the web material such that any of the aforementioned positioning can be achieved, including for example placement of the fastening component entirely between the distances D1 and D2 on the final article, at a distance from the front waist edge 114 that is entirely less than distance D4 from the front waist edge 114, closer to the outboard lateral edge 152 of the section of web material than to the inboard lateral edge 153 of the section of web material, and/or such that the fastening component lies tangent to, or along, the front leg band line. Registration may be done in the machine direction (i.e., placing fastening components at specific MD distances or with reference to specific MD positions), cross-machine direction, with reference to cut lines (discussed below), fold lines or margins, leg elastic band lines (discussed above) or any combination thereof. Registration can be achieved by any suitable process. In some embodiments, sensors are used to recognize registration feature(s) on the material. The sensor may communicate the presence of the registration feature to a controller to identify the appropriate position or process timing for placement of the fastening component. Registration features may include printed graphics, variance in web path, optimal markers and/or physical discontinuities such as notches, protrusions, depressions, or holes formed in a substrate and/or components. Some registration processes are disclosed in U.S. Pat. Nos. 8,145,343; 8,145,338; 8,145,344; 8,244,393; 8,712,573; 8,712,574; and 9,429,929 and U.S. Pat. App. No. 2019-0060135.

If edge margins of the strip of web material 500 are to be cut away from the strip of web material, the strip of web material 500 may be conveyed along the machine direction to side edge cutting equipment 515 configured to cut away edge margins. Such cutting may be desired, for example, when needed to impart a consistent cross-direction width and neat side edges to the strip of web material 500 and/or to provide profiled side edges 516 to the strip, and thereby to provide profiled tab portions and distal ends to the front ear portions of the combination belt structure 550. If the combination belt structure is to be provided with front ear portions folded over as suggested in the description above, the strip of web material 500 may be conveyed along the machine direction to folding equipment 520, configured to fold side margin portions 522 over the strip 500, along machine direction fold lines 521. Folding the side margin portions 522 over the strip 500 prior to cutting away of individual combination belt structures 550, may in some circumstances be more simple, efficient and reliable than folding over front ear portions of separate individual belt structures. The folded side margin portions may subsequently become the folded front ear portions of the combination belt structures 550.

At any point in the manufacturing of combination belt structures 550 following the first step, the strip of web material may be gathered on a roll for efficient storage and transport to downstream manufacturing steps, at which time the strip may be unrolled for further manufacturing steps. For example, the strip of web material may be gathered on a roll following application of fastening components 511; or following side edge cutting; or following folding along machine direction fold lines 521 as described above, or following completion of all of these steps.

Figure 20A:
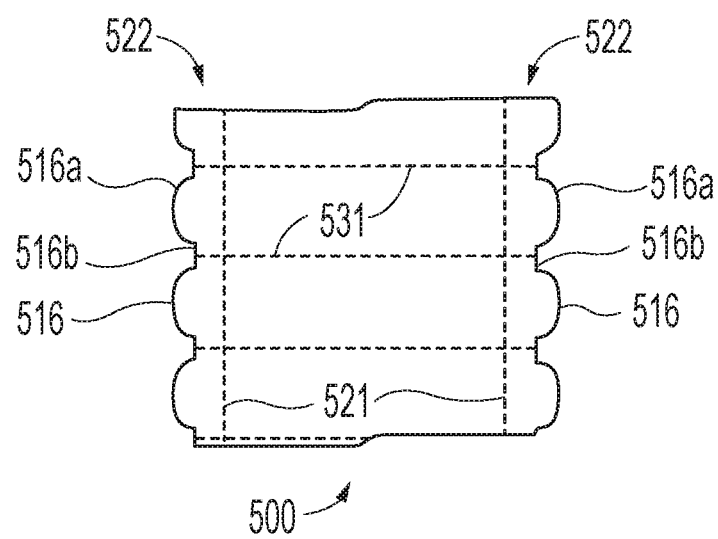
FIGS. 20A and 20B are schematic illustrations of alternative side edge profiles, fold lines and cut lines for manufacturing belt structures.
Figure 20B:
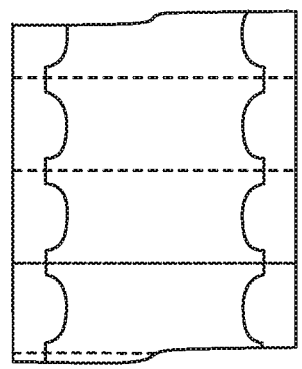

Referring to FIG. 19, the processed strip of web material 500 may be (if gathered on a roll, unrolled and) conveyed along the machine direction MD to cross-direction cutting equipment 530 configured to cut away individual combination belt structures 550 along cross direction cut lines 531. This step may be incorporated as part of the manufacturing process for diapers, in which a continuous supply of the combination belt structures are provided on a roll prior to cutting and separation into individual belt structures 550 for application to diaper chasses.

Where profiled side edges are to be provided, the side edge cutting equipment 515 may be configured to cut material 500 along any profile shape desired for the tab and distal end portions of the front ear portions of the combination belt structures 550. In some circumstances, it may be desired to provide a series of connecting convexly-curved side edge profiles as suggested in FIGS. 5, 18 and 19, which will result in convexly-curved tab and distal end portions of front ears. Referring to FIGS. 20A and 20B, in some circumstances it may be desired to provide a series of side edge profiles that include alternating convex portions 516*a* and concave portions 516*b*. This alternating convex/concave side edge profile configuration may provide the manufacturer with some room for process variation in location of cross direction cut lines 531, such that a minor machine-direction variance or deviation from the specified location of cut lines 531 is unlikely to result in the creation of a sharply pointed, laterally protruding, esthetically undesirable sliver of material at an outside end/corner of a front ear intended to have a simple rounded tab profile. (For purposes of the immediately-preceding description, the term "convex" is not limited to a rounded curve, but also includes an outward-directed (relative the machine direction axis of the strip of web material) sharp corner in a profile, and the term "concave" is not limited to a rounded curve, but also includes an inward-directed (relative the machine direction axis of the strip of web material) sharp corner in a profile. Thus, a side edge cut having an alternating/reversing step-wise profile with sharp corners would have "convex" and "concave" portions).

Figure 21:
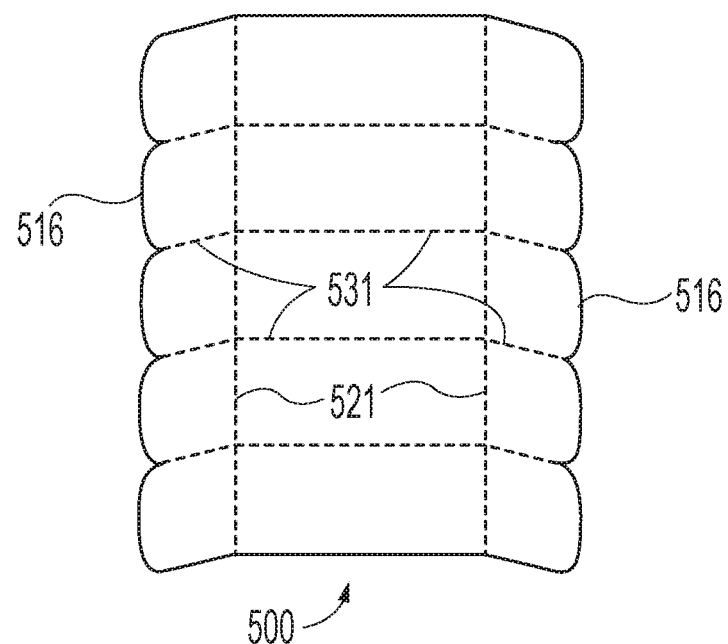
FIGS. 21-23 are schematic illustrations of various alternative cut lines and fold lines located on a strip of web material, for manufacturing belt structures.
Figure 22:
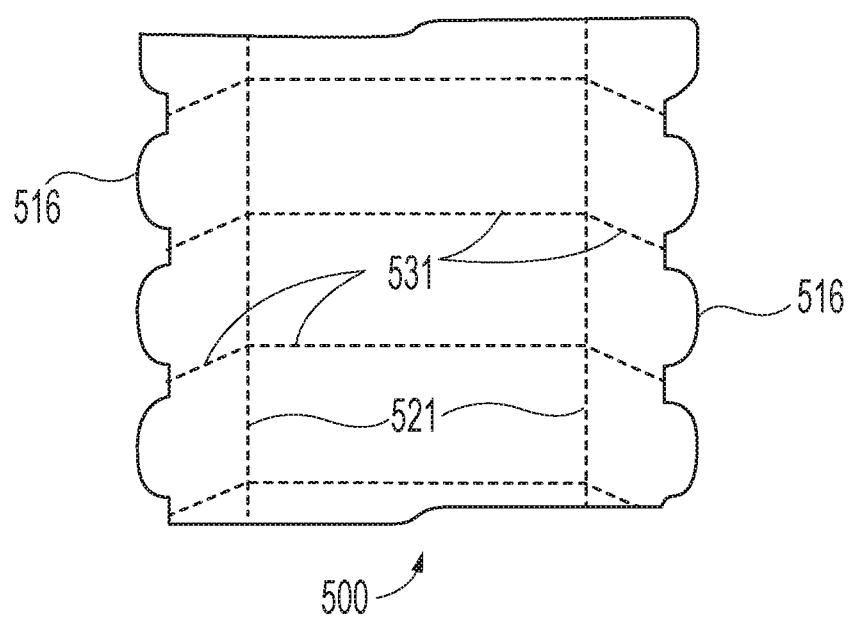
Figure 23:
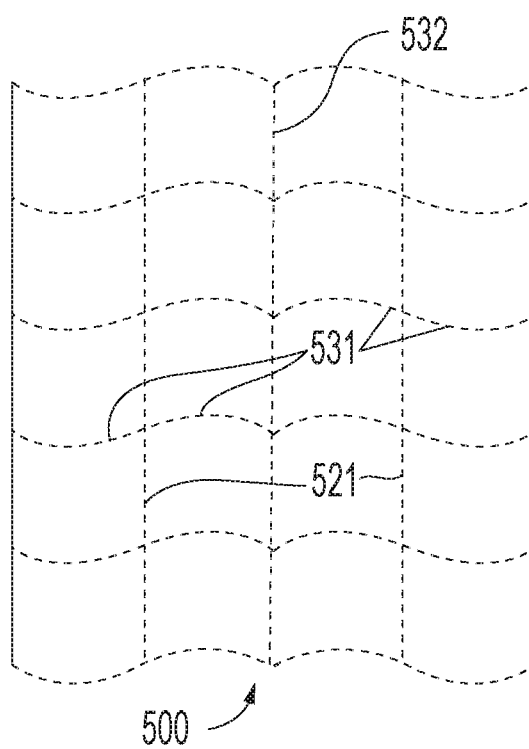

FIGS. 21-23 depict alternative possible folding and cutting arrangements which may be desired in varying circumstances. When the manufacturer desires that the front ears 155 extend from the chassis downward toward the lateral axis of the diaper as described above, a pattern of cross-direction cut lines 531 such as depicted in FIG. 21 or 22 may be desired. It will be appreciated that cut lines 531 provide for nested shapes of belt structures to be successively cut away from the strip of web material 500, minimizing material waste. In some examples, cut lines 531 may be curved rather than straight or straight-sectioned as depicted.

FIG. 23 depicts a possible cutting arrangement that may be used to produce a pair of left and right belt structures with front ears such as are depicted in FIG. 4. An additional machine direction cut line 532 is included, to separate the left and right portions.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Test Methods

Hysteresis Test Method

Obtain samples of subject material sufficient to provide for a gauge length of at least 15 mm along the direction of stretch in the Test, and should be of a constant width (perpendicular to the direction of stretch in the Test) of at least 5 mm.

The Hysteresis Test can be used to various specified strain values. The Hysteresis Test utilizes a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The samples are conditioned for 24 hours prior to testing.

Test Protocol

1. Select the appropriate grips and load cell. The grips must have flat surfaces and must be wide enough to grasp the sample along its full width. Also, the grips should provide adequate force to ensure that the sample does not slip during testing. The load cell is selected so that the tensile response from the sample tested is between 25% and 75% of the capacity of the load cell used.

2. Calibrate the tester according to the manufacturer's instructions.

3. Set the distance between the grips (gauge length) at 15 mm.

4. Place the sample in the flat surfaces of the grips such that the uniform width lies along a direction perpendicular to the gauge length direction. Secure the sample in the upper grips, let the sample hang slack, then close the lower grips. Set the slack preload at 0.02 N/cm. This means that the data collection starts when the slack is removed (at a constant crosshead speed of 10 mm/min) with a force of 0.02 N/cm. Strain is calculated based on the adjusted gauge length ($l_{ini}$), which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length times 100.

5(a) First cycle loading: Pull the sample to the specified strain (herein, 100%) at a constant cross head speed of 100 mm/min Report the stretched sample length between the grips as $l_{max}$.

5(b) First cycle unloading: Hold the sample at the specified strain for 30 seconds and then return the crosshead to its starting position (0% strain or initial sample length, $l_{ini}$) at a constant cross head speed of 100 mm/min Hold the sample in the unstrained state for 1 minute.

5(c) Second cycle loading: Pull the sample to the specified strain at a constant cross head speed of 100 mm/min.

5(d) Second cycle unload: Next, return the crosshead to its starting position (i.e. 0% strain) at a constant cross head speed of 100 mm/min.

A computer data system records the force exerted on the sample during the test as a function of applied strain. From the resulting data generated, the following quantities are reported (note that loads are reported as force divided by the width of the sample and do not take into account the thickness of the sample):

i. Length of sample between the grips at a slack preload of 0.02 N/cm ($l_{ini}$) to the nearest 0.001 mm.

ii. Length of sample between the grips on first cycle at the specified strain ($l_{max}$) to the nearest 0.001 mm.

iii. Length of sample between the grips at a second cycle load force of 0.02 N/cm ($l_{ext}$) to the nearest 0.001 mm.

iv. % set, which is defined as $(l_{ext}-l_{ini})/(l_{max}-l_{ini})*100\%$ to the nearest 0.01%.

The testing is repeated for six separate samples and the average and standard deviation reported.

The Hysteresis Test can be suitably modified depending on the expected attributes and/or properties of the particular material sample to be measured. For example, the Test can be suitably modified where a sample of the length and width specified above are not available from the subject diaper.

Stiffness Test Method

The Stiffness Test measures the bending properties of a sample.

Identify the waist region by measuring the length of the article along the longitudinal centerline from the front waist edge to the rear waist edge, and dividing said length into three equal sections. For samples in the front waist region, remove the specimens from the front third of the article. For samples in the rear waist region, remove the specimens from the last third of the article.

Cut a rectangular section of material measuring at least 30 mm by 50 mm, excluding any primary first components or secondary first components. Cut the specimen such that the 50 mm dimension in the longitudinal direction of the article and parallel to the longitudinal axis. Maintain the longitudinal direction relative to the product and note the garment facing side of the specimen. If the specimen does not allow these dimensions, smaller samples can be used.

Specimens are conditioned at 23° C.±3° C. and 50%±2% relative humidity two hours prior to testing.

The bending properties of a sample are measured on a constant rate of extension tensile tester (a suitable instrument is the MTS Alliance using Testworks 4.0 Software, as available from MTS Systems Corp., Eden Prairie, Minn.) using a load cell for which the forces measured are within 10% to 90% of the limit of the cell. All testing is performed in a room controlled at 23° C.±3° C. and 50%±2% relative humidity.

The bottom stationary fixture of the tensile tester consists of two bars 3.175 mm in diameter by 60 mm in length, made of polished stainless steel each mounted on its own fork in linear ball bearing to reduce COF affect. These two bars are mounted horizontally, aligned front to back and parallel to each other, with top radii of the bars vertically aligned. Furthermore, the fixture allows for the two bars to be move horizontally away from each other on a track so that a gap can be set between them while maintaining their orientation. The top movable fixture consists of a third bar also 3.175 mm in diameter by 60 mm in length, made of polished stainless steel mounted on a fork in linear ball bearing to reduce COF affect. When in place the bar of the top fixture is parallel to, and aligned front to back with the bars of the bottom fixture. Both fixtures include an integral adapter appropriate to fit the respective position on the tensile tester frame and lock into position such that the bars are orthogonal to the motion of the crossbeam of the tensile tester.

Set the gap between the bars of the lower fixture to 5 mm±0.1 mm (center of bar to center of bar) with the upper bar centered at the midpoint between the lower bars. Set the gage (bottom of top bar to top of blower bars) to 3 mm.

Measure the caliper of each specimen, using a digital caliper (e.g. Ono Sokki GS-503 or equivalent) fitted with a 25 mm diameter foot that applies a confining pressure of 0.1 PSI. Read the caliper (mm) 5 sec after resting the foot on the sample and record to the nearest 0.01 mm.

Program the tensile tester for a compression test, to move the crosshead down at a rate of 0.5 mm/sec until the upper bar touches the top surface of the specimen, then continue for an additional 8 mm collecting force (N) and displacement mm data at 200 Hz, and return the crosshead to its original gage. Orient specimens with garment facing side toward the upper bar. Load the specimen such that it spans the two lower bars with its lateral centerline centered under the upper bar and its longitudinal centerline aligned to the center point of the upper bar's length. Zero the crosshead and load cell. Start the run and collect data.

Construct a graph of force (N) verses displacement (mm). Read the Maximum Peak Force (N) from the graph and record to the nearest 0.1 N. Report the slope as N/mm to the nearest 0.1 N/mm.

Measures are repeated in like fashion for 3 specimens from the same location. The arithmetic average slope of the three specimens is reported as the sample's Stiffness to the nearest 0.1 N/mm A difference in magnitude between two samples can be determined using the following equation:

$$\Delta \text{Magnitude} = \frac{\text{Stiffness for Sample } A - \text{Stiffness for Sample } B}{\text{Stiffness for Sample } A}$$

What is claimed is:

1. A method for forming successive individual combination belt structures each comprising fastening components, the method comprising:
    providing a machine-direction continuous strip of web material having a pair of machine-direction outer side edges, opposing side margin portions, and a cross-direction width therebetween, wherein at least a portion of the web material is patterned to comprise loops;
    continuously affixing successive pairs of fastening components to the web material as it moves along a machine direction, wherein the fastening components are positioned laterally inboard of the opposing side margin portions, and wherein the fastening components respectively comprise hooks configured to fasten to the loops;
    folding over the side margin portions of the web material or individual combination belt structures in the cross-direction about machine-direction fold lines, so that in each combination belt structure at least one side margin portion at least partially covers the affixed fastening component;
    cutting individual combination belt structures from the web material along predominately cross-direction cut lines, each combination belt structure comprising at least one of the affixed fastening component.

2. The method of claim 1, wherein the folding occurs after the cutting.

3. The method of claim 1, wherein the folding occurs prior to the cutting.

4. The method of claim 1, further comprising:
cutting successive pairs of profiled side edges between the pair of machine-direction outer edges.

5. The method of claim 4, wherein the cutting the successive pairs of profiled side edges occurs prior to the affixing.

6. The method of claim 4, wherein the profiled side edges have convex and concave curved portions.

7. The method of claim 1, wherein the fastening components in a pair of fastening components are spaced a defined distance apart from each other.

8. The method of claim 1, further comprising registering the fastening components with specific locations on the web material.

9. A method for forming successive individual belt structures for diapers, comprising:
providing a machine-direction continuous strip of web material having a pair of machine-direction outer side edges and a cross-direction width therebetween;
affixing successive pairs of fastening components to the web material laterally inboard of opposing side margin portions;
cutting successive pairs of profiled tab portions in the pair of machine-direction outer side edges;
folding over the opposing side margin portions of the web material in the cross direction about machine-direction fold lines, so that in each belt structure at least one side margin portion at least partially covers the affixed fastening component; and
cutting individual belt structures from the web material along predominately cross-direction cut lines, each belt structure comprising cut portions of the folded-over side margins.

10. The method of claim 9, wherein at least a portion of the web material is patterned bonded.

11. The method of claim 9, wherein the profiled tab portions have convex and concave curved portions.

12. The method of claim 9, wherein the profiled tab portions form a grip portion.

13. The method of claim 9, further comprising gathering a machine-direction length of the strip of web material with the folded-over side margins on a roll, following the folding, and unrolling the length from the roll, prior to the cutting the individual belt structures.

14. A method for forming successive combination belt structures for diapers, comprising the steps of:
providing a machine-direction continuous strip of web material having a pair of machine-direction outer side edges and a cross-direction width therebetween;
affixing successive pairs of fastening components to the web material laterally inboard of opposing side margin portions;
cutting successive pairs of profiled tab portions in the pair of machine-direction outer edges, wherein each profiled tab portion comprises a first convexity, a second convexity and a concavity disposed between the first and second convexities;
folding over the opposing side margin portions of the web material in the cross direction about machine-direction fold lines, so that in each belt structure at least one side margin portion at least partially covers the affixed fastening component; and
cutting individual combination belt structures from the web material along predominately cross-direction cut lines, each combination belt structure comprising profiled side edges.

15. The method of claim 14, wherein the the cutting the successive pairs of profiled tab portions comprises forming the first convexity to extend outboard of the second convexity in the cross-machine direction.

16. The method of claim 14, wherein at least a portion of the web material is patterned to comprises loops configured to engage with hooks.

17. The method of claim 14, further comprising providing a signal at least proximate to the first convexity, wherein the signal comprises a color, texture, pattern, and/or indicia.

* * * * *